US006835544B2

(12) United States Patent
Mathews et al.

(10) Patent No.: US 6,835,544 B2
(45) Date of Patent: Dec. 28, 2004

(54) METHODS OF SCREENING FOR COMPOUNDS THAT BIND TO ACTIVIN RECEPTOR

(75) Inventors: Lawrence W. Mathews, Ann Arbor, MI (US); Wylie W. Vale, Jr., La Jolla, CA (US); Kunihiro Tsuchida, San Diego, CA (US)

(73) Assignee: The Salk Institute for Biological Studies, LaJolla, CA (US)

( * ) Notice: Subject to any disclaimer, the term of this patent is extended or adjusted under 35 U.S.C. 154(b) by 105 days.

(21) Appl. No.: 09/742,684

(22) Filed: Dec. 19, 2000

(65) Prior Publication Data

US 2001/0039036 A1 Nov. 8, 2001

Related U.S. Application Data

(60) Division of application No. 08/476,123, filed on Jun. 7, 1995, now Pat. No. 6,162,896, which is a continuation-in-part of application No. 08/300,584, filed on Sep. 2, 1994, now Pat. No. 5,885,794, which is a continuation of application No. 07/880,220, filed on May 8, 1992, now abandoned, which is a continuation-in-part of application No. 07/773,229, filed on Oct. 9, 1991, now abandoned, which is a continuation-in-part of application No. 07/698,709, filed on May 10, 1991, now abandoned.

(51) Int. Cl.$^7$ .......................... G01N 33/53; C12Q 1/68; C07K 14/715
(52) U.S. Cl. .............................. 435/7.1; 435/6; 530/351
(58) Field of Search ...................... 435/6, 7.1; 530/350, 530/351

(56) References Cited

U.S. PATENT DOCUMENTS 5,538,892 A * 7/1996 Donahoe et al. ............ 435/325
5,614,609 A * 3/1997 Ib a nez et al. ............ 530/350

OTHER PUBLICATIONS

Kondo et al, Identification of the two types of specific receptor for activin/EDF expressed on Friend leukemia and embryonal carcinoma cells. Biochem. Biophys. Res. Commun. 161:1267–1272, 1989.*
Campen et al, Characterization of activin A binding sites on the human leukemia cell line K562. Biochem. Biophys. Res. Commun. 157: 844–849, 1988.*
Konno, Y., et al. Enzymatic properties of a novel Phorbol ester receptor/Protein Kinase, nPKC. J. Biochem. (Tokyo) 106(4):673–678, 1989.*
Beckmann and Kadesch, "The leucine zipper of TFE3 dictates helix–loop–helix dimerization specificity" *Genes & Development* 5:1057–1066 (1991).
Blackwell and Weintraub, "Differences and Similarities in DNA–Binding Preferences of MyoD and E2A Protein Complexes Revealed by Binding Site Selection" *Science* 250:1104–1110 (1990).
Campen and Vale, "Characterization of Activin a Binding Sites on the Human Leukemia Cell Line K562" *Biochem. Biophys. Res. Comm.* 157(2):844–849 (1988).

Càrcamo et al., "Type I Receptors Specify Growth–Inhibitory and Transcriptional Responses to Transforming Growth Factor β and Activin" *Molecular and Cellular Biology* 14(6):3810–3821 (1994).
Centrella et al., "Activin–A Binding and Biochemical Effects in Osteoblast–Enriched Cultures from Fetal–Rat Parietal Bone" *Molecular and Cellular Biology* 11(1):250–258 (1991).
Cooper et al., "Detection and Quantification of Phosphotyrosine in Proteins" *Methods in Enzymology* 99:387–402 (1983).
Featherstone and Russell, "Fission yeast p107$^{wee1}$ mitotic inhibitor is a tyrosine/serine kinase" *Nature* 349:808–811 (1991).
Feng and Doolittle, "Progressive Sequence Alignment as a Prerequisite to Correct Phylogenetic Trees" *J. Mol. Evol.* 25:351–360 (1987).
Fitch and Margoliash, "Construction of Phylogenetic Trees" *Science* 155:279–284 (1967).
Gearing et al., "Expression cloning of a receptor for human granulocyte–macrophage colony–stimulating factor" *EMBO Journal* 8(12):3667–3676 (1989).
Georgi et al., "daf–1, a *C. elegans* Gene Controlling Dauer Larva Development, Encodes a Novel Receptor Protein Kinase" *Cell* 61:635–645 (1990).
Hanks and Quinn, "Protein Kinase Catalytic Domain Sequence Database: Identification of Conserved Features of Primary Structure and Classification of Family Members" *Methods in Enzymology* 200:38–62 (1991).
Hanks et al., "The Protein Kinase Family: Conserved Features and Deduced Phylogeny of the Catalytic Domains" *Science* 241:42–52 (1988).

Primary Examiner—Brenda Brumback
Assistant Examiner—Ruixiang Li
(74) Attorney, Agent, or Firm—Stephen E. Reiter; Foley & Lardner

(57) ABSTRACT

In accordance with the present invention, there are provided novel receptor proteins characterized by having the following domains, reading from the N-terminal end of said protein:

an extracellular, ligand-binding domain, a hydrophobic, trans-membrane domain, and an intracellular, receptor domain having serine kinase-like activity.

The invention receptors optionally further comprise a second hydrophobic domain at the amino terminus thereof. The invention receptor proteins are further characterized by having sufficient binding affinity for at least one member of the activin/TGF-β superfamily of polypeptide growth factors such that concentrations of $\leq 10$ nM of said polypeptide growth factor occupy $\geq 50\%$ of the binding sites of said receptor protein. A presently preferred member of the invention superfamily of receptors binds specifically to activins, in preference to inhibins, transforming growth factor-β, and other non-activin-like proteins. DNA sequences encoding such receptors, assays employing same, as well as antibodies derived therefrom, are also disclosed.

10 Claims, 6 Drawing Sheets

OTHER PUBLICATIONS

Hino et al., "Characterization of Cellular Receptors for Erythroid Differentiation Factor on Murine Erythroleukemia Cells" *J. Biol. Chem.* 264(17):10309–10314 (1989).

Howell et al., "STY, a Tyrosine–Phosphorylating Enzyme with Sequence Homology to Serine/Threonine Kinases" *Molecular and Cellular Biology* 11(1):568–572 (1991).

Kintner, C., "Effects of Altered Expression of the Neural Cell Adhesion Molecule, N–CAM, on Early Neural Development in Xenopus Embryos" *Neuron* 1:545–555 (1988).

Kintner and Melton, "Expression of Xenopus N–CAM RNA in ectoderm is an early response to neural induction" *Development* 99:311–325 (1987).

Kondo et al., "Identification of the Two Types of Specific Receptor for Activin/EDF Expressed on Friend Leukemia and Embryonal Carcinoma Cells" *Biochem. Biophys. Res. Comm.* 161(3):1267–1272 (1989).

Kozak M., "An analysis of 5'-noncoding sequences from 699 vertebrate messenger RNAs" *Nucleic Acids Research* 15:8125–8148 (1987).

Krieg and Melton, "In Vitro RNA Synthesis with SP6 RNA Polymerase" *Methods in Enzymology* 155:397–415 (1987).

Kyte and Doolittle, "A Simple Method for Displaying the Hydropathic Character of a Protein", *J. Mol. Biol.* 157:105–132 (1992).

Mason et al., "Activin B: Precursor Sequences, Genomic Stucture and in Vitro Activities" *Molecular Endocrinology* 3(9):1352–1358 (1989).

Massague et al., "TGF–β Receptors and TGF–β Binding Proteoglycans: Recent Progress in Identifying Their Funtional Properties" *Ann. N. Y. Acad. Sci.* 593:59–73 (1990).

Mathews and Vale, "Expression Cloning of an Activin Receptor, a Predicted Transmembrane Serine Kinase" *Cell* 65:973–982 (1991).

Melton et al., "Efficient in vitro synthesis of biologically active RNA and RNA hybridization probes from plasmids containing a bacteriophage SP6 promoter" *Nucleic Acids Research* 12:7035–7056 (1984).

Mine et al., "Stimulation of Glucose Production by Activin–A in Isolated Rat Hepatocytes" *Endocrinology* 125(2):586–591 (1989).

Munson and Rodbard, "Ligand: A Versatile Computerized Approach for Charaterization of Ligand–Binding Systems" *Analytical Biochemistry* 107:220–239 (1980).

Nakamura et al., "Association of Activin–Binding Protein with Cell Surface" *Abstracts; J. Cell Biol* 111:351a (1990).

Pearson and Lipman, "Improved tools for biological sequence comparison" *Proc. Natl. Acad. Sci. USA* 85:2444–2448 (1988).

Saito et al., "Production of Activin–Binding Protein by Rat Granulosa Cells in vitro" *Biochem. and Biophysical Res. Comm.* 176(1):413–422 (1991).

Scatchard, G., "The Attractions of Proteins for Small Molecules and Ions" *Ann. N. Y. Acad. Sci.* 51:660–672 (1949).

Smith and Johnson, "Single–step purification of polypeptide expressed in *Escherichia coli* as fusions with glutathione S–transferase" *Gene* 67:31–40 (1988).

Stern et al., "Spk1, a New Kinase from *Saccharomyces cerevisiae*, Phosphorylates Proteins on Serine, Threonine, and Tyrosine" *Molecular and Cellular Biology* 11(2):987–1001 (1991).

Sugino et al., "Identification of a Specific Receptor for Erythroid Differentiation Factor on Follicular Granulosa Cell" *J. Biol. Chem.* 263(30):15249–15252 (1988).

Vale et al., "Purification and characterization of an FSH releasing protein from porcine ovarian follicular fluid" *Nature* 321:776–779 (1986).

Vale et al., "The Inhibin/Activin Family of Hormones and Growth Factors" *Handbook of Experimental Pharmacology* Sporn and Roberts eds., 95/II:211–247 (1990).

von Heijne, G., "Transcending the impenetrable: how proteins come to terms with membranes" *Biochimic et Biophysica Acta* 947:307–333 (1988).

Walker and Zhang, "Relationship of a putative receptor protein kinase from maize to the S–locus glycoproteins of Brassica" *Nature* 345:743–746 (1990).

Wong et al., "Human GM–CSF: Molecular Cloning of the Complementary DNA and Purification of the Natural and Recombinant Proteins" *Science* 228:810–815 (1985).

* cited by examiner

Divide a cDNA library in a mammalian expression vector into pools of 1000 clones, prepare DNA from each pool Transfect COS cells directly on microscope slides Bind [125I] activin A, wash cells, fix, dip in photographic emulsion Subdivide bacteria from positive pool and rescreen; repeat until receptor clone is pure

FIG. 4

METHODS OF SCREENING FOR COMPOUNDS THAT BIND TO ACTIVIN RECEPTOR

RELATED APPLICATIONS

This application is a divisional application of U.S. application No. 08/476,123, filed Jun. 7, 1995, now issued as U.S. Pat. No. 6,162,896 on Dec. 19, 2000, which is a continuation-in-part of U.S. application Ser. No. 08/300,584, filed Sep. 2, 1994, now issued as U.S. Pat. No. 5,885,794 on Mar. 23, 1999, which is a continuation of U.S. application Ser. No. 07/880,220, filed May 8, 1992, now abandoned, which is a continuation-in-part of U.S. application Ser. No. 07/773,229, filed Oct. 9, 1991, now abandoned, which is, in turn, a continuation-in-part of U.S. application Ser. No. 07/698,709, filed May 10, 1991, now abandoned.

ACKNOWLEDGEMENT

This invention was made with Government support under Grant Numbers HD 13527 and DK 26741, awarded by the National Institutes of Health. The Government has certain rights in this invention.

FIELD OF THE INVENTION

The present invention relates to receptor proteins, DNA sequences encoding same, and various uses therefor.

BACKGROUND OF THE INVENTION

Activins are dimeric proteins which have the ability to stimulate the production of follicle stimulating hormone (FSH) by the pituitary gland. Activins share a common subunit with inhibins, which inhibit FSH secretion.

Activins are members of a superfamily of polypeptide growth factors which includes the inhibins, the transforming growth factors-β (TGF-β), Mullerian duct inhibiting substance, the *Drosophila decapentaplegic* peptide, several bone morphogenetic proteins, and the Vg-related peptides.

As a result of their extensive anatomical distribution and multiple biological actions, members of this superfamily of polypeptide growth factors are believed to be involved in the regulation of numerous biological processes. Activin, for example, is involved in the proliferation of many tumor cell lines, the control of secretion and expression of the anterior pituitary hormones (e.g., FSH, GH and ACTH), neuron survival, hypothalamic oxytocin secretion, erythropoiesis, placental and gonadal steroidogenesis, early embryonic development, and the like.

Other members of the activin/TGF-β superfamily of polypeptide growth factors are involved in the regulation of cell function and cell proliferation for numerous cell types, in adults and embryos. For example, cells which are subject to regulation by one or more members of the activin/TGF-β superfamily of polypeptide growth factors include mesenchymal cells, muscle cells, skeletal cells, immune cells, hematopoietic cells, steroidogenic cells, endothelial cells, liver cells, epithelial cells, and the like.

Chemical cross-linking studies with a number of cell types suggests that multiple binding sites (i.e., receptors) exist on the surface of cells. However, little is known about the structure of these receptors, or about the second messenger signalling systems that they employ. It would be desirable, therefore, if the nature of these poorly characterized receptor proteins could be more fully understood.

BRIEF DESCRIPTION OF THE INVENTION

In accordance with the present invention, we have identified and characterized members of a new superfamily of receptor proteins which comprise three distinct domains: an extracellular, ligand-binding domain, a hydrophobic, transmembrane domain, and an intracellular, receptor domain having serine kinase-like activity.

Also provided are DNAs encoding the above-described receptor proteins, and antibodies thereto, as well as bioassays, therapeutic compositions containing such proteins and/or antibodies, and applications thereof.

The DNAs of the invention are useful as probes for the identification of additional members of the invention superfamily of receptor proteins, and as coding sequences which can be used for the recombinant expression of the invention receptor proteins, or functional fragments thereof. The invention receptor proteins, and antibodies thereto, are useful for the diagnosis and therapeutic management of carcinogenesis, wound healing, disorders of the immune, reproductive, or central nervous systems, and the like.

BRIEF DESCRIPTION OF THE FIGURES

FIG. 4 presents a comparison between activin receptor and daf-1 [a C. elegans gene encoding a putative receptor protein kinase (with unknown ligand); see Georgi, et al., Cell 61: 635–645 (1990)]. Conserved residues between the activin receptor and daf-1 are highlighted; conserved kinase domain residues are designated with an "*".

DETAILED DESCRIPTION OF THE INVENTION

In accordance with the present invention, there is provided a novel superfamily of receptor protein(s) characterized by having the following domains, reading from the N-terminal end of said protein:

an extracellular, ligand-binding domain, a hydrophobic, trans-membrane domain, and an intracellular domain having serine kinase-like activity.

The novel receptor protein(s) of the invention optionally further comprise a second hydrophobic domain at the amino terminus thereof.

Figure 1:
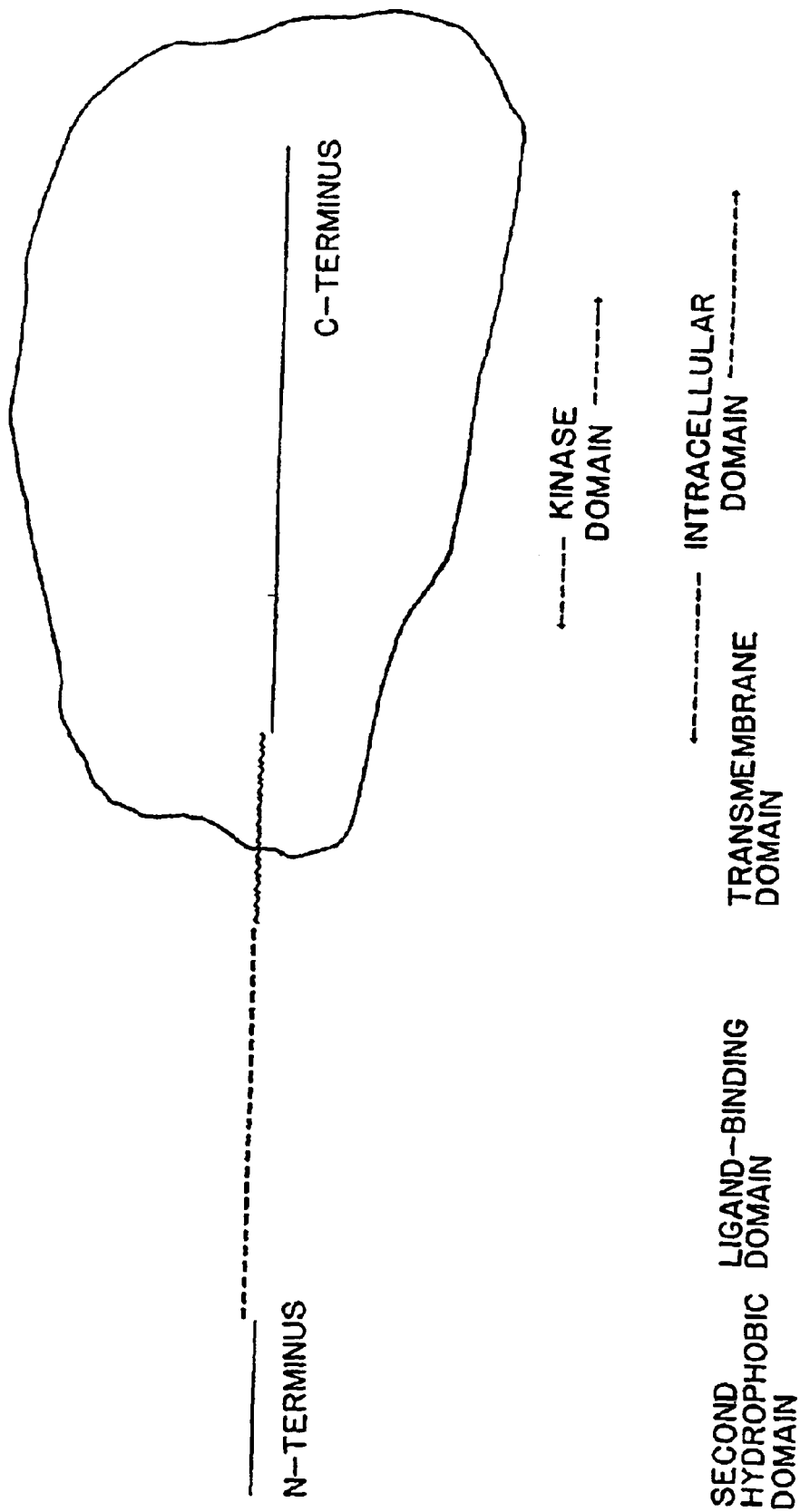
FIG. 1 is a schematic diagram of receptors of the invention and the various domains thereof.
Figure 2:
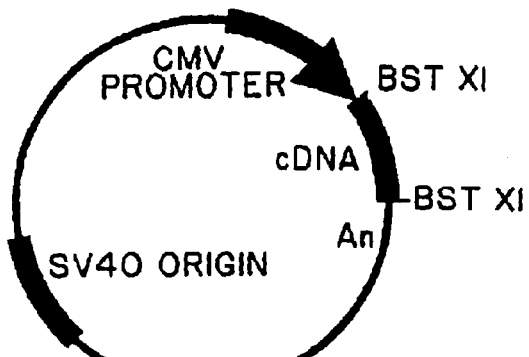
FIG. 2 outlines the strategy used for expression cloning of a receptor of the activin/TGF-β receptor superfamily.
Figure 2:
Figure 2:
Figure 2:

As employed herein, the phrase "extracellular, ligand-binding domain" refers to that portion of receptors of the invention which has a high affinity for ligand, and which, when associated with a cell, resides primarily outside of the cell membrane. Because of its location, this domain is not exposed to the processing machinery present within the cell, but is exposed to all components of the extracellular medium. See FIG. 1.

As employed herein, the phrase "hydrophobic, trans-membrane domain" refers to that portion of receptors of the invention which traverses the cell membrane, and serves as a "bridge" between the extracellular and intracellular domains of the receptor. The hydrophobic nature of this domain serves to anchor the receptor to the cell membrane. See FIG. 1.

As employed herein, the phrase "intracellular domain having serine kinase-like activity" refers to that portion of receptors of the invention which resides within the cytoplasm, and which embodies the catalytic functionality characteristic of all receptors of the invention. See FIG. 1.

The optional second hydrophobic domain, positioned at the amino terminus of receptors of the invention, comprises a secretion signal sequence which promotes the intracellular transport of the initially expressed receptor protein across the Golgi membrane. See FIG. 1.

Members of the invention superfamily of receptors can be further characterized as having sufficient binding affinity for at least one member of the activin/TGF-β superfamily of polypeptide growth factors such that concentrations of ≦10 nM of said polypeptide growth factor occupy ≧50% of the binding sites of said receptor protein.

Binding affinity (which can be expressed in terms of association constants, Ka, or dissociation constants, Kd) refers to the strength of interaction between ligand and receptor, and can be expressed in terms of the concentration of ligand necessary to occupy one-half (50%) of the binding sites of the receptor. A receptor having a high binding affinity for a given ligand will require the presence of very little ligand to become at least 50% bound (hence the Kd value will be a small number); conversely, receptor having a low binding affinity for a given ligand will require the presence of high levels of ligand to become 50% bound (hence the Kd value will be a large number).

Reference to receptor protein "having sufficient binding affinity such that concentrations of said polypeptide growth factor less than or equal to 10 nM (i.e., ≦10 nM) occupy ≧50% (i.e., greater than or equal to one-half) of the binding sites of said receptor protein" means that ligand (i.e., polypeptide growth factor) concentration(s) of no greater than about 10 nM are required in order for the ligand to occupy at least 50% of the active sites of said receptor (preferably about 0.1–1.0 nM of said receptor), with much lower ligand concentrations typically being required. Presently preferred receptors of the present invention have a binding affinity such that ligand concentration(s) in the range of only about 100–500 pM are required in order to occupy (or bind to) at least 50% of the receptor binding sites, wherein the receptor concentration is preferably about 0.1–1.0 nM.

Members of the invention superfamily of receptors can be divided into various subclasses, based on the approximate size of the crosslinked complexes obtained when radiolabeled activin is chemically crosslinked to cell extracts [see, for example, Example VI below, or Mathews and Vale in Cell 65:973–982 (1991)]. Type I activin/TGF-β receptors are those which form a crosslinked complex of about 65 kD with activin; Type II receptors are those which form a crosslinked complex of about 80–85 kD with activin; while Type III, Type IV and the like receptors are those which form crosslinked complexes with activin having molecular weights greater than about 100 kD.

Each member of a given subclass is related to other members of the same subclass by the high degree of homology (e.g., >80% overall amino acid homology; frequently having >90% overall amino acid homology) between such receptors; whereas members of a given subclass differ from members of a different subclass by the lower degree of homology (e.g., at least about 30% up to 80% overall amino acid homology; with in the range of about 40% up to 90% amino acid homology specifically in the kinase domains thereof) between such receptors. Typically, related receptors have at least 50% overall amino acid homology; with at least about 60% amino acid homology in the kinase domains thereof. Preferably, related receptors are defined as those which have at least 60% overall amino acid homology; with at least about 70% amino acid homology in the kinase domains thereof.

Based on the above criteria, the receptors described herein are designated Type II receptors, with the first discovered Type II receptor (i.e., the mouse-derived activin receptor) being designated ActRII, while subsequently identified Type II receptors which are not homologs of ActRII (because while clearly related by size and some sequence homology, they differ sufficiently to be considered as variants of ActRII), are designated ActRIIB, ActRIIC, etc.

Presently preferred members of the invention superfamily of receptors are further characterized by having a greater binding affinity for activins than for inhibins. Such receptors are frequently also observed to have:

substantially no binding affinity for transforming growth factors-β, and substantially no binding affinity for non-activin-like proteins or compounds.

Additional members of the invention superfamily of receptors are further characterized by having a greater binding affinity for inhibins than for activins or TGF-βs.

Additional members of the invention superfamily of receptors are further characterized by having a greater binding affinity for TGF-βs than for activins or inhibins.

As employed herein, "activin" refers to activin A (a homodimer of two inhibin $β_A$ subunits), activin B (a homodimer of two inhibin $β_B$ subunits), activin AB (a heterodimer composed of one inhibin $β_A$ subunit and one inhibin $β_B$ subunit); "inhibin" refers to inhibin A (composed of the inhibin α subunit and an inhibin $β_A$ subunit), inhibin B (composed of the inhibin α subunit and an inhibin $β_B$ subunit); "transforming growth factor β or TGF-β" refers to TGF-β1 (a homodimer of two TGF-β1 subunits), TGF-β2 (a homodimer of two TGF-β2 subunits), TGF-β3 (a homodimer of two TGF-β3 subunits), TGF-β4 (a homodimer of two TGF-β4 subunits), TGF-β5 (a homodimer of two TGF-β5 subunits), TGF-β1.2 (a heterodimer of one TGF-β1 subunit and one TGF-β2 subunit), and the like.

Transforming growth factors-β (TGF-βs) are members of the activin/TGF-β superfamily of polypeptide growth factors. TGF-βs are structurally related to activins, sharing at least 20–30% amino acid sequence homology therewith. TGF-βs and activins have a substantially similar distribution pattern of cysteine residues (or substitution) throughout the peptide chain. Furthermore, both polypeptides, in their active forms, are dimeric species.

As employed herein, the term "non-activin-like" proteins refers to any protein having essentially no structural similarity with activins (as defined broadly herein).

Preferred members of the invention superfamily of receptors comprise those having in the range of about 500 amino acids, and are further characterized by having the following designated sizes for each of the domains thereof, reading from the N-terminal end of said receptor:

the extracellular, ligand-binding domain preferably will have in the range of about 88–118 amino acids, the hydrophobic, trans-membrane domain preferably will have in the range of about 23–28 amino acids, beginning at the carboxy terminus of the extracellular domain, and the intracellular domain having kinase-like activity preferably will have in the range of about 345–360 amino acids, beginning at the carboxy terminus of the hydrophobic, trans-membrane domain.

Receptors of the invention optionally further comprise a second hydrophobic domain having in the range of about 16–30 amino acids at the extreme amino terminus thereof (i.e., at the amino terminus of the extracellular, ligand-binding domain). This domain is a secretion signal sequence, which aids the transport of invention receptor(s) across the cell membrane. Exemplary secretion signal sequences include amino acids 1–19 of Sequence ID No. 1, amino acids 1–20 of Sequence ID No. 3, amino acids 1–25 of Sequence ID No. 11, and the like. Such secretion signal sequences can be encoded by such nucleic acid sequences as nucleotides 71–127 of Sequence ID No. 1, nucleotides 468–527 of Sequence ID No. 3, nucleotides 72–146 of Sequence ID No. 11, and the like.

Members of the invention superfamily of receptors can be obtained from a variety of sources, such as, for example, pituitary cells, placental cells, hematopoietic cells, brain cells, gonadal cells, liver cells, bone cells, muscle cells, endothelial cells, epithelial cells, mesenchymal cells, kidney cells, and the like. Such cells can be derived from a variety of organisms, such as, for example, human, mouse, rat, ovine, bovine, porcine, frog, chicken, fish, mink, and the like.

Presently preferred amino acid sequences encoding receptor proteins of the invention include the sequence set forth in Sequence ID No. 2 (which represents a mouse activin receptor amino acid sequence), a modified form of Sequence ID No. 2 wherein the arginine at residue number 39 is replaced by a lysine, the isoleucine at residue number 92 is replaced by a valine, and the glutamic acid at residue number 288 is replaced by a glutamine (which modified form of Sequence ID No. 2 is referred to hereinafter as Sequence ID No 16", and represents a human activin receptor amino acid sequence), the sequence set forth as Sequence ID No. 4 (which represents a Xenopus activin receptor amino acid sequence), and Sequence ID No. 12 (which represents a rat activin receptor-like kinase amino acid sequence) as well as functional, modified forms thereof. Those of skill in the art recognize that numerous residues of the above-described sequences can be substituted with other, chemically, sterically and/or electronically similar residues without substantially altering the biological activity of the resulting receptor species.

In accordance with another embodiment of the present invention, there is provided a soluble, extracellular, ligand-binding protein, further characterized by:

having sufficient binding affinity for at least one member of the activin/TGF-β superfamily of polypeptide growth factors such that concentrations of ≦10 nM of said polypeptide growth factor occupy ≧50% of the binding sites on said receptor protein, and having at least about 30% sequence identity with respect to:

the sequence of amino acids 20–134 set forth in Sequence ID No. 2;

the sequence of amino acids 20–134 set forth in Sequence ID No. 16;

the sequence of amino acids 21–132 set forth in Sequence ID No. 4; or the sequence of amino acids 26–113 set forth in Sequence ID No. 12.

Presently preferred soluble, extracellular, ligand-binding proteins contemplated by the present invention can be further characterized by having at least about 50% sequence identity with respect to:

the sequence of amino acids 20–134 set forth in Sequence ID No. 2;

the sequence of amino acids 20–134 set forth in Sequence ID No. 16;

the sequence of amino acids 21–132 set forth in Sequence ID No. 4; or the sequence of amino acids 26–113 set forth in Sequence ID No. 12;

with the presently most preferred soluble, extracellular, ligand-binding proteins having at least about 80% sequence identity with respect to the above-referenced fragments of Sequence ID Nos. 2, 4 or 12.

Members of the class of soluble, ligand-binding proteins contemplated by the present invention may be divided into various subclasses, as previously described, wherein members of one subclass may have a greater binding affinity for activins than for inhibins and/or TGF-βs; or alternatively, members of another subclass may have a greater binding affinity for inhibins than for activins and/or TGF-βs; or alternatively, members of yet another subclass may have a greater binding affinity for TGF-βs than for activins and/or inhibins. It is, of course, understood by those of skill in the art, that members of more than one subclass may have a greater binding affinity for one member of the activin/TGF-β superfamily of polypeptide growth factors, relative to other members of the superfamily.

Presently preferred soluble, extracellular, ligand-binding proteins of the present invention are further characterized by:

having a greater binding affinity for activins than for inhibins, having substantially no binding affinity for transforming growth factors-β, and having substantially no binding affinity for non-activin-like proteins.

Presently preferred soluble, extracellular, ligand-binding proteins of the present invention typically comprise in the range of about 88–118 amino acids.

Especially preferred soluble, extracellular, ligand-binding proteins of the invention are those having substantially the same amino acid sequence as that set forth as:

residues 20–134 of Sequence ID No. 2;
residues 20–134 of Sequence ID No. 16;
residues 21–132 of Sequence ID No. 4; or
residues 26–113 of Sequence ID No. 12.

As employed herein, the term "substantially the same amino acid sequence" refers to amino acid sequences having at least about 80% identity with respect to the reference amino acid sequence, and will retain comparable functional and biological properties characteristic of the protein encoded by the reference amino acid. Preferably, proteins having "substantially the same amino acid sequence" will have at least about 90% amino acid identity with respect to the reference amino acid sequence; with greater than about 95% amino acid sequence identity being especially preferred.

The above-described soluble proteins can be employed for a variety of therapeutic uses, e.g., to block receptors of the invention from affecting processes which the receptors would otherwise mediate. The presence of the soluble proteins of the invention will compete with functional ligand for the receptor, preventing the formation of a functional receptor-ligand complex, thereby blocking the normal regulatory action of the complex.

In accordance with yet another embodiment of the present invention, there are provided antibodies generated against the above-described soluble proteins and receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins as antigens for antibody production.

In accordance with still another embodiment of the present invention, there are provided methods for modulating the transcription trans-activation of receptor(s) of the invention by contacting said receptor(s) with a modulating, effective amount of the above-described antibodies.

The soluble proteins of the invention, and the antibodies of the invention, can be administered to a subject employing standard methods, such as, for example, by intraperitoneal, intramuscular, intravenous, or subcutaneous injection, implant or transdermal modes of administration, and the like. In addition, methods such as transfection with viral or retroviral vectors encoding the invention compositions. One of skill in the art can readily determine dose forms, treatment regiments, etc, depending on the mode of administration employed.

In accordance with a further embodiment of the present invention, there are provided DNA sequences which encode the above-described soluble proteins and receptor proteins. Optionally, such DNA sequences, or fragments thereof, can be labeled with a readily detectable substituent (to be used, for example, as a hybridization probe).

The above-described receptor(s) can be encoded by numerous DNA sequences, e.g., a DNA sequence having a contiguous nucleotide sequence substantially the same as:

nucleotides 128–1609 of Sequence ID No. 1 (which encodes a mouse activin receptor);

nucleotides 128–1609 of Sequence ID No. 15 (which encodes a human activin receptor);

nucleotides 528–1997 of Sequence ID No. 3 (which encodes a Xenopus activin receptor);

nucleotides 147–1550 of Sequence ID No. 11 (which encodes a rat activin receptor); or variations of any of the above sequences which encode the same amino acid sequences, but employ different codons for some of the amino acids.

As employed herein, the term "substantially the same as" refers to DNA having at least about 70% homology with respect to the nucleotide sequence of the DNA fragment with which subject DNA is being compared. Preferably, DNA "substantially the same as" a comparative DNA will be at least about 80% homologous to the comparative nucleotide sequence; with greater than about 90% homology being especially preferred.

Another DNA which encodes a receptor of the invention is one having a contiguous nucleotide sequence substantially the same as:

nucleotides 71–1609 of Sequence ID No. 1 (which encodes a precursor-form of a mouse activin receptor);

nucleotides 71–1609 of Sequence ID No. 15 (which encodes a precursor-form of a human activin receptor);

nucleotides 468–1997 of Sequence ID No. 3 (which encodes a precursor form of a Xenopus activin receptor); or nucleotides 72–1550 of Sequence ID No. 11 (which encodes a precursor form of a rat activin receptor); or variations of any of the above sequences which encode the same amino acid sequences, but employ different codons for some of the amino acids.

Yet another DNA which encodes the above-described receptor is one having a contiguous nucleotide sequence substantially the same as set forth in Sequence ID No. 1, Sequence ID No. 15, Sequence ID No. 3, or Sequence ID No. 11.

In accordance with a further embodiment of the present invention, the receptor-encoding cDNAs can be employed to probe library(ies) (e.g., cDNA, genomic, and the like) for additional sequences encoding novel receptors of the activin/TGF-$\beta$ superfamily. Such screening is initially carried out under low-stringency conditions, which comprise a temperature of less than about 42° C., a formamide concentration of less than about 50%, and a moderate to low salt concentration. Presently preferred conditions for such screening comprise a temperature of about 37° C., a formamide concentration of about 20%, and a salt concentration of about 5x standard saline citrate (SSC; 20xSSC contains 3M sodium chloride, 0.3M sodium citrate, pH 7.0). Such conditions will allow the identification of sequences which have a substantial degree of similarity with the probe sequence, without requiring perfect homology for the identification of a stable hybrid. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe.

In accordance with yet another embodiment of the present invention, there is provided a method for the recombinant production of receptor(s) of the invention by expressing the above-described DNA sequences in suitable host cells.

The use of a wide variety of recombinant organisms has been described for the production of peptides. One of skill in the art can readily determine suitable hosts (and expression conditions) for use in the recombinant production of the peptides of the present invention. Yeast hosts, bacterial hosts, mammalian hosts, and the like can be employed. Regulatory sequences capable of controlling the expresseion of invention peptides are well known for each of these host systems, as are growth conditions under which expression occurs.

In accordance with a further embodiment of the present invention, there is provided a binding assay employing receptors of the invention, whereby a large number of compounds can be rapidly screened to determine which compounds, if any, are capable of binding to the receptors of the invention. Then, more detailed assays can be carried out with those compounds found to bind, to further determine whether such compounds act as agonists or antagonists of invention receptors.

Another application of the binding assay of the invention is the assay of test samples (e.g., biological fluids) for the presence or absence of members of the activin/TGF-β superfamily of polypeptide growth factors. Thus, for example, serum from a patient displaying symptoms related to pathway(s) mediated by members of the activin/TGF-β superfamily of polypeptide growth factors can be assayed to determine if the observed symptoms are perhaps caused by over- or under-production of such polypeptide growth factor.

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with a still further embodiment of the present invention, there are provided bioassays for evaluating whether test compounds are capable of acting as agonists or antagonists of receptor(s) of the present invention.

The bioassays of the present invention involve evaluating whether test compounds are capable of acting as either agonists or antagonists for members of the invention superfamily of receptors, or functional modified forms of said receptor protein(s). The bioassay for evaluating whether test compounds are capable of acting as agonists comprises:
 (a) culturing cells containing:
  DNA which expresses said receptor protein(s) or functional modified forms of said receptor protein(s), and
  DNA encoding a hormone response element operatively linked to a reporter gene;
  wherein said culturing is carried out in the presence of at least one compound whose ability to induce transcription activation activity of receptor protein is sought to be determined, and thereafter
 (b) monitoring said cells for expression of the product of said reporter gene.

The bioassay for evaluating whether test compounds are capable of acting as antagonists for receptor(s) of the invention, or functional modified forms of said receptor(s), comprises:
 (a) culturing cells containing:
  DNA which expresses said receptor protein(s), or functional modified forms of said receptor protein(s), and
  DNA encoding a hormone response element operatively linked to a reporter gene
  wherein said culturing is carried out in the presence of: increasing concentrations of at least one compound whose ability to inhibit transcription activation of said receptor protein(s) is sought to be determined, and
  a fixed concentration of at least one agonist for said receptor protein(s), or functional modified forms of said receptor protein(s); and thereafter (b) monitoring in said cells the level of expression of the product of said reporter gene as a function of the concentration of said compound, thereby indicating the ability of said compound to inhibit activation of transcription.

Host cells contemplated for use in the bioassay(s) of the present invention, include CV-1 cells, COS cells, and the like; reporter and expression plasmids employed typically also contain the origin of replication of SV-40; and the reporter and expression plasmids employed also typically contain a selectable marker.

The hormone response element employed in the bioassay (s) of the present invention can be selected from, for example, mouse mammary tumor virus long terminal repeat (MTV LTR), mammalian growth hormone promoter, and the reporter gene can be selected from chloramphenicol acetytransferase (CAT), luciferase, β-galactosidase, and the like.

The cells can be monitored for the level of expression of the reporter gene in a variety of ways, such as, for example, by photometric means [e.g., by colorimetry (with a colored reporter product such as β-galactosidase), by fluorescence (with a reporter product such as luciferase), etc), by enzyme activity, and the like.

Compounds contemplated for screening in accordance with the invention bioassays include activin- or TGF-β-like compounds, as well as compounds which bear no particular structural or biological relatedness to activin or TGF-β.

As employed herein, the phrase "activin- or TGF-β-like compounds" includes substances which have a substantial degree of homology (at least 20% homology) with the amino acid sequences of naturally occurring mammalian inhibin alpha and $\beta_A$ or $\beta_B$ chains (either singly or in any combination) as well as alleles, fragments, homologs or derivatives thereof which have substantially the same qualitative biological activity as mammalian inhibin, activin, or TGF-β. Examples of activin- or TGF-β-like compounds include activin A (a homodimer of two inhibin $\beta_A$ subunits), activin B (a homodimer of two inhibin $\beta_B$ subunits), activin AB (a heterodimer composed of one inhibin $\beta_A$ subunit and one inhibin $\beta_B$ subunit), inhibin A (composed of the inhibin a subunit and an inhibin $\beta_A$ subunit), inhibin B (composed of the inhibin α subunit and an inhibin $\beta_B$ subunit), TGF-β1 (a homodimer of two TGF-61 subunits), TGF-β2 (a homodimer of two TGF-β2 subunits), TGF-β3 (a homodimer of two TGF-β3 subunits), TGF-β4 (a homodimer of two TGF-β4 subunits), TGF-β5 (a homodimer of two TGF-β5 subunits), TGF-β1.2 (a heterodimer of one TGF-β1 subunit and one TGF-β2 subunit), and the like.

Examples of compounds which bear no particular structural or biological relatedness to activin or TGF-β, but which are contemplated for screening in accordance with the bioassays of the present invention, include any compound that is capable of either blocking the action of the invention receptor peptides, or promoting the action of the invention receptor peptides, such as, for example, alkaloids and other heterocyclic organic compounds, and the like.

The method employed for cloning the receptor(s) of the present invention involves expressing, in mammalian cells, a cDNA library of any cell type thought to respond to members of the activin/TGF-β superfamily of polypeptide growth factors (e.g., pituitary cells, placental cells, fibroblast cells, and the like). Then, the ability of the resulting mammalian cells to bind a labeled receptor ligand (i.e., a labeled member of the activin/TGF-β superfamily of polypeptide growth factors) is determined. Finally, the desired cDNA insert(s) are recovered, based on the ability of that cDNA, when expressed in mammalian cells, to induce (or enhance) the binding of labeled receptor ligand to said cell.

In addition to the above-described applications of the receptor proteins and DNA sequences of the present invention, the receptor or receptor-encoding compositions of the invention can be used in a variety of ways. For example, since activin is involved in many biological processes, the activin receptor (or antibodies thereto) can be applied to the modulation of such biological processes. For example, the stimulation of FSH release by activin can either be enhanced (for example, by supplying the subject with increased amounts of the activin receptor, relative to the amount of endogenous receptor, e.g., by transfecting the subject with a tissue specific activin-encoding construct), or depressed (e.g., by administration to a subject of antibodies to the activin receptor, thereby preventing formation of activin-receptor complex, which would then act to stimulate the release of FSH). Thus, the compositions of the present invention can be applied to the control of fertility in humans, domesticated animals, and animals of commercial interest.

As another example, the effect of activin on mitosis of red and white blood cells can be modulated, for example, by administering to a subject (employing suitable means of administration) a modulating, effective amount of activin receptor (which would enhance the ability of activin present in the cell to modulate mitosis). Alternatively, one could administer to a subject an antibody to the activin receptor (or a portion thereof), which would reduce the effect of activin by blocking the normal interaction between activin and activin receptor.

As additional examples of the wide utility of the invention compositions, receptors and/or antibodies of the invention can be used in such areas as the diagnosis and/or treatment of activin-dependent tumors, enhancing the survival of brain neurons, inducing abortion in livestock and other domesticated animals, inducing twinning in livestock and other domesticated animals, and so on.

As still further examples of the wide utility of the invention compositions, agonists identified for TGF-β specific receptors can be used to stimulate wound healing, to suppress the growth of TGF-β-sensitive tumors, to suppress immune response (and thereby prevent rejection of transplanted organs), and the like. Antagonists or the soluble, ligand-binding domain derived from TGF-β receptors can be used to block endogenous TGF-β, thereby promoting liver regeneration and stimulating some immune responses.

It can be readily seen, therefore, that the invention compositions have utility in a wide variety of diagnostic, clinical, veterinary and research applications.

The invention will now be described in greater detail by reference to the following non-limiting examples.

EXAMPLES

Recombinant human (rh) activin A, rh activin B, and rh inhibin A were generously provided by Genentech, Inc. Porcine TGF-β1 was obtained from R+D Systems.

Double-stranded DNA was sequenced by the dideoxy chain termination method using the Sequenase reagents from US Biochemicals. Comparison of DNA sequences to databases was performed using the FASTA program [Pearson and Lipman, Proc. Natl. Acad. Sci. USA 85: 2444–2448 (1988)).

Example I

Construction and Subdivision of AtT20 cDNA Library

Polyadenylated RNA was prepared from AtT20 cells using the Fast Track reagents from InVitrogen. cDNA was commercially synthesized and ligated into the plasmid vector pcDNA1 using non-palindromic BstXI linkers, yielding a library of approximately $5 \times 10^6$ primary recombinants. The unamplified cDNA library was plated at 1000 clones per 100 mm plate, then scraped off the plates, frozen in glycerol and stored at −70°.

Activin suppresses adrenocorticotrophic hormone (ACTH) secretion by both primary anterior pituitary cell cultures [Vale et al., Nature 321: 776–779 (1986)] and AtT20 mouse corticotropic cells. Because AtT20 cells possess activin receptors indistinguishable from those on other cell types (based on binding affinity measurements with activin A), these cells were chosen to be the source of cDNA for transfection. A cDNA library of approximately $5 \times 10^6$ independent clones from AtT20 cells was constructed in the mammalian expression vector, pcDNA1, and screened using an expression cloning approach [Gearing et al., EMBO J. 8, 3667–3676 (1989)] based on the ability to detect activin binding to single transfected cells. The library was divided into pools of 1000 clones, DNA was prepared from each pool of clones and transiently transfected into COS cells, and the cells screened for the capacity to bind iodinated activin A. Binding was assessed by performing the transfections and binding reactions directly on chambered microscope slides, then dipping the slides in photographic emulsion and analyzing them under a microscope. Cells which had been transfected with an activin receptor cDNA, and consequently bound radioactive activin, were covered with silver grains. DNA from pools of clones were analyzed either singly or in groups of three. Of 300 pools (approximately 300,000 clones) assayed in this manner, one group of three generated two positive cells when transfected into COS cells. The positive pool (#64) was identified by transfecting and analyzing DNA from each pool of 1000 singly, and then was further fractionated until a single clone (pmActR1) was purified which generated $>10^4$ positive cells after transfection (see Table 1).

TABLE 1

Purification of the activin receptor clone from the AtT20 library

| Pool | Clones/pool | Positive cells/slide |
|---|---|---|
| 62, 63, 64 | 3×1000 | 2 |
| 64 | 1000 | 1–3 |
| 64-51 | 400 | 4–10 |
| 64-51-R10; 64-51-C13 | 20 | 25–40 |
| pmActR1 | 1 | $>10^4$ |

Figure 3:
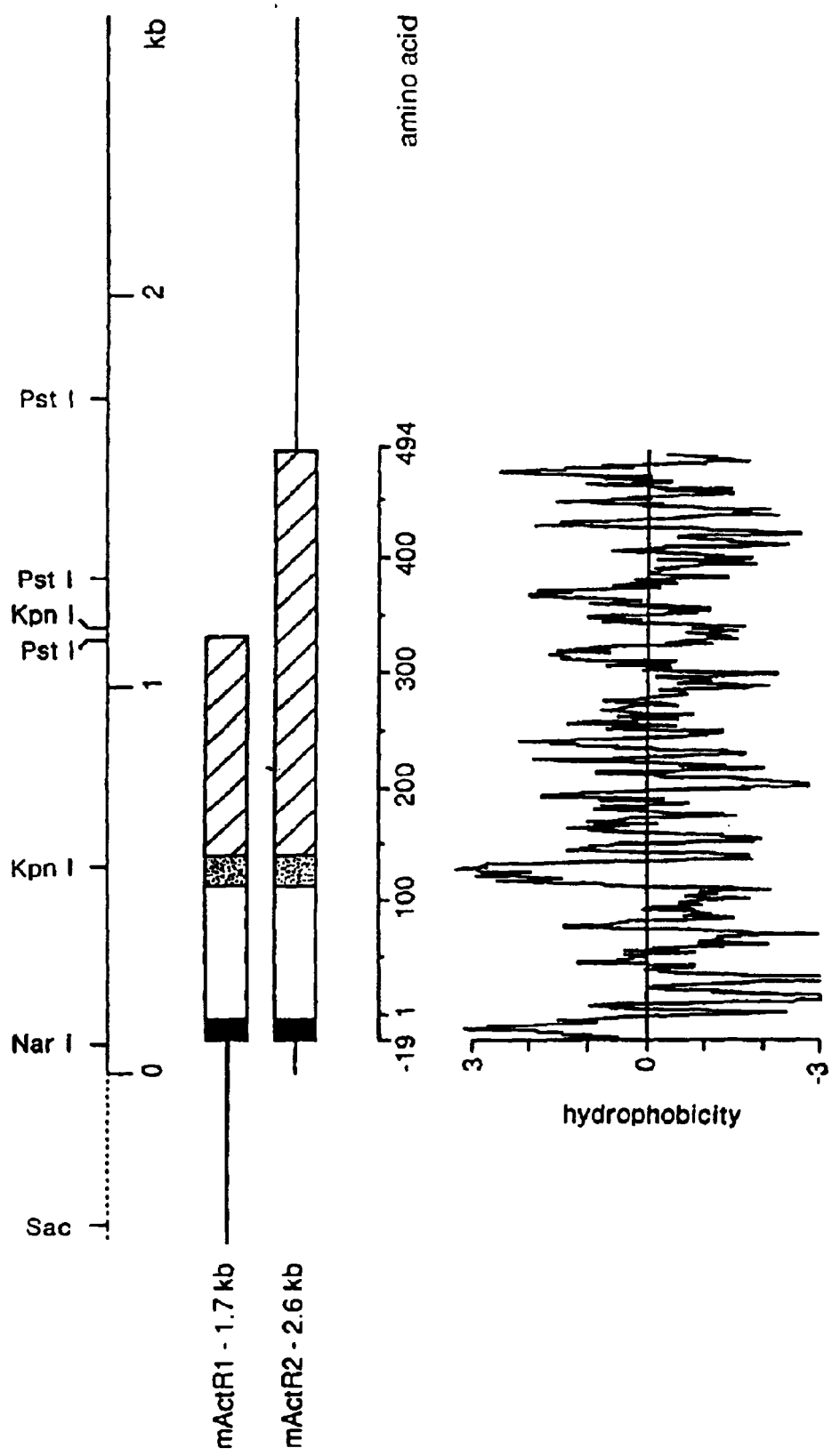
FIG. 3 is a schematic of two mouse activin receptor clones. The top line of the figure is a restriction map, in kb, of mActR1 and mActR2, with numbering starting from bp 1 of mActR2. The dotted line in the figure represents 5' untranslated sequences present only in mActR1. The middle lines present a schematic representation of two activin receptor cDNA clones. Boxes represent coding sequences—black is the signal peptide, white is the extracellular ligand-binding domain, gray is the transmembrane, and the intracellular kinase domain is hatched. Amino acids are numbered beneath the schematics.

The total number of transfected cells capable of binding $^{125}$I activin A in a field of $2 \times 10^5$ COS cells was counted for pools of clones at each stage of the purification process.

pmActR1 contained a 1.7 kb insert, coding for a protein of 342 amino acids (FIG. 3); however, it was incomplete on the 3' end, thus the last 17 amino acids were encoded by vector sequences. In order to obtain the entire sequence, the AtT20 library was rescreened by hybridization with the 1.6 kb SacI-PstI fragment (FIG. 3). Screening $6 \times 10^5$ colonies yielded one additional positive clone (pmActR2) which had a 2.6 kb insert and contained the entire coding sequence for the mouse activin receptor (FIG. 3). The nucleic acid sequence and the deduced amino acid sequence of the insert in pmActR2 are set forth in Sequence ID No. 1.

Example II

COS Cell Transfection

Aliquots of the frozen pools of clones from Example I were grown overnight in 3 ml cultures of terrific broth, and mini-prep DNA prepared from 1.5 ml using the alkaline lysis method [Maniatis et al. Molecular Cloning (Cold Spring Harbor Laboratory (1982)]. 1/10 of the DNA from a mini-prep (10 Ml of 100 Ml) was used for each transfection.

$2 \times 10^5$ COS cells were plated on chambered microscope slides (1 chamber—Nunc) that had been coated with 20 μg/ml poly-D-lysine and allowed to attach for at least 3 hours. Cells were subjected to DEAE-Dextran mediated transfection as follows. 1.5 ml of serum-free Dulbecco's Modified Eagle's medium (DME) containing 100 mM chloroquine was added to the cells. DNA was precipitated in 200 ml DME/chloroquine containing 500 mg/ml DEAE-Dextran, then added to the cells. The cells were incubated at 37° for 4 hours, then the media was removed and the cells were treated with 10% DMSO in HEPES buffered saline for 2 minutes. Fresh media was added and the cells assayed 3 days later. For transfections with the purified clone, $2.5 \times 10^6$ cells were transfected in 100 mm dishes with 5 μg purified DNA. The total transfection volume was 10 ml, and the DNA was precipitated in 400 μl.

Example III

Binding Assay

Cells were washed 2× with HEPES buffered saline (HDB) containing 0.1% BSA, then incubated for 90 minutes at 220 in 0.5 ml HDB, 0.1% BSA containing $7 \times 10^5$ cpm $^{125}$I activin A (approximately 7 ng, 500 pM). The cells were then washed 3× with cold HDB, fixed for 15 minutes at 22° in 2.5% glutaraldehyde/HDB and washed 2× with HDB. The chambers were then peeled off the slides, and the slides dehydrated in 95% ethanol, dried under vacuum, dipped in NTB2 photographic emulsion (Kodak) and exposed in the dark at 40 for 3 days. Following development of the emulsion, the slides were dehydrated in 95% ethanol, stained with eosin and coverslipped with DPX mountiant (Electron Microscopy Sciences). The slides were analyzed under darkfield illumination using a Leitz microscope.

Example IV

Subdivision of Positive Pool

Of 300 pools screened (each pool containing about 1000 cDNAs), one positive pool (#64), which produced two positive cells, was identified. Bacteria from the frozen stock of this positive pool (#64) were replated at approximately 400 clones per plate, replica plates were made, and DNA was prepared from each subpool and analyzed employing the binding assay described above. Several positive subpools were found, which generated from 4–10 positive cells per slide. The bacteria from the replica plate of one positive subpool were picked onto a grid, and DNA prepared from pools of clones representing all the rows and all the columns, as described by Wong (Science 228:810–815 (1985)]. The identification of one positive row and one positive column unambiguously identified a single clone, which when transfected yielded $>10^4$ positive cells/$2 \times 10^5$ cells.

Example V

Figure 5A:
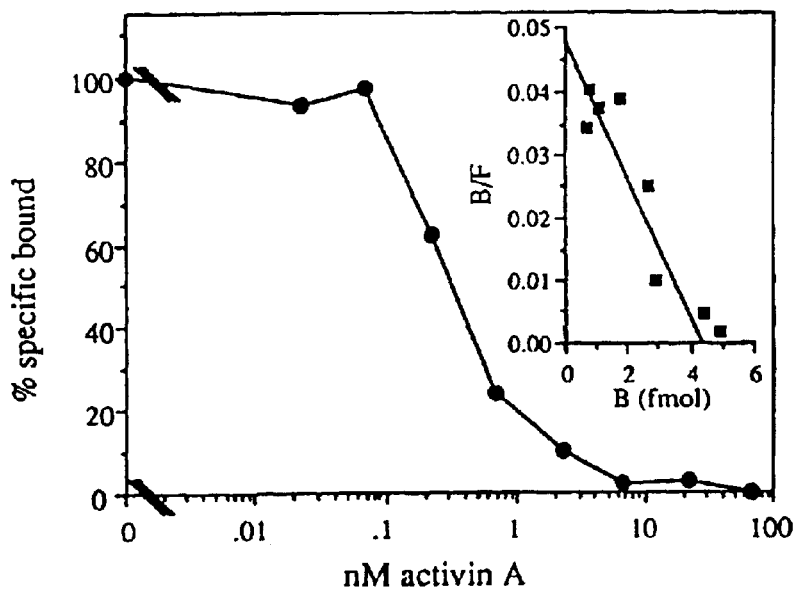
FIG. 5A summarizes results of $^{125}$I activin A binding to COS cells transfected with pmActR1. Binding was competed with unlabeled activin A. For the runs reported herein, total binding was 4.6% of input cpm, non-specific binding was 0.9% of input cpm, and therefore the specific binding was 3.7% of input cpm. Data are shown as % specific binding, normalized to 100%. The inset presents a Scatchard analysis of the data [Ann. NY Acad. Sci. 51: 660–672 (1979)].

Radioreceptor Assay $10^5$ COS cells transfected with either pmActR1 or pmActR2, or $10^6$ untransfected COS cells, were plated in 6 well dishes and allowed to grow overnight. The cells were washed 2× with HDB, 0.1% BSA, and incubated at 220 for 90 minutes in 0.5 ml HDB, 0.1% BSA containing 100,000 cpm (approximately 1 ng, 75 pM) $^{125}$I activin A (5 μg activin A was iodinated by chloramine T oxidation to a specific activity of 50–90 μCi/μg; iodinated activin A was purified on a 0.7×20 cm G-25 column) and varying amounts of unlabeled competitor hormone. Following binding, the cells were washed 3× with cold HDB, solubilized in 0.5 ml 0.5 N NaOH, removed from the dish and radioactivity was measured in a gamma counter. Data presented in FIG. 5 are expressed as % specific binding, where 100% specific binding is the difference between binding in the absence of competitor and binding in the presence of a 100 fold molar excess of unlabeled activin A. Binding parameters were determined using the program LIGAND (Munson P. J. and Rodbard, D., Anal. Biochem. 107:220–259 (1980)].

Example VI

Chemical Cross-Linking $2 \times 10^6$ COS cells, or $5 \times 10^6$ AtT20 cells, were washed 2× with HDB, scraped off the dish, incubated for 90 minutes at 220 under constant rotation in 0.5 ml HDB containing $7 \times 10^5$ cpm (approximately 500 pM) $^{125}$I activin A with or without 500 ng (37 nM) unlabeled activin A. Cells were diluted with 1 ml HDB, pelleted by centrifugation and resuspended in 0.5 ml HDB. Disuccinimidyl suberate (DSS; freshly dissolved in DMSO) was added to 500 μM, and the cells incubated at 0° for 30 minutes. The cross-linking was terminated by addition of 1 ml 50 mM Tris-HCl pH 7.5, 100 mM NaCl, then the cells were pelleted by centrifugation, resuspended in 100 μl So mM Tris-HCl pH 7.5, 1% Triton X-100 and incubated at 0° for 60 minutes. The samples were centrifuged 5 minutes at 13,000×g, and the Triton-soluble supernatants analyzed by SDS-PAGE using 8.5% polyacrylamide gels. The gels were dried and subjected to autoradiography for 4–14 days.

Example VII

RNA Blot Analysis

Total RNA was purified from tissue culture cells and tissues using LiCl precipitation. 20 μg total RNA was run on 1.2% agarose, 2.2M formaldehyde gels, blotted onto nylon membranes (Hybond—NEN), and hybridized with a 0.6 kb KpnI fragment (see FIG. 3) which had been labeled with $^{32}$P by random priming using reagents from US Biochemicals. Hybridization was performed at 420 in 50% formamide, and the filters were washed at 650 in 0.2×SSC.

Example VIII

Sequence Analysis

Full length mouse activin receptor clone encodes a protein of 513 amino acids, with a 5' untranslated region of 70 bp and a 31 untranslated region of 951 bp. pmActR2 does not contain a poly A tail, although it does have a potential poladenylylation site at bp 2251. The insert in clone pmActR1 had an additional 551 bp of 5' untranslated sequence, was identical in the overlapping range, and stopped at the 3' end at base 1132 of pmActR2. The first methionine codon (ATG), at bp 71, in pmActR2 is in a favorable context for translation initiation (Kozak, M., Nucl. Acids Res. 15:8125–8148 (1987)], and is preceded by an in-frame stop codon. pmActR1 contains 3 additional ATGs in the 5' untranslated region; however, none of these is in an appropriate context for initiation, and all are followed by in-frame stop codons. While this unusually long 5' leader sequence may have functional significance, it is clearly not necessary for proper expression, because pmActR2, which lacks most of that sequence, can be functionally expressed in COS cells (see below).

Hydropathy analysis using the method of Kyte and Doolittle [J. Mol. Biol. 157:105–132 (1982)] revealed two hydrophobic regions: a 10 amino acid stretch at the amino terminus assumed to be a single peptide, and a single putative 26 residue membrane-spanning region between amino acids 119–142 (see FIG. 1 and Sequence ID No. 2). The signal peptide contains the conserved n-, h- and c-domains common to signal sequences; the site of cleavage of the signal peptide, before $Ala^1$, is predicted based on rules described by von Heijne [Biochim. Biophys. Act. 947:307–333 (1988)]. As is common for the cytoplasmic side of membrane-spanning domains, the predicted transmembrane region is closely followed by two basic amino acids. The mature mouse activin receptor is thus predicted to be a 494 amino acid type I membrane protein of Mr 54 kDa, with a 116 amino acid N-terminal extracellular ligand binding domain, and a 346 amino acid intracellular signalling domain.

Figure 4:
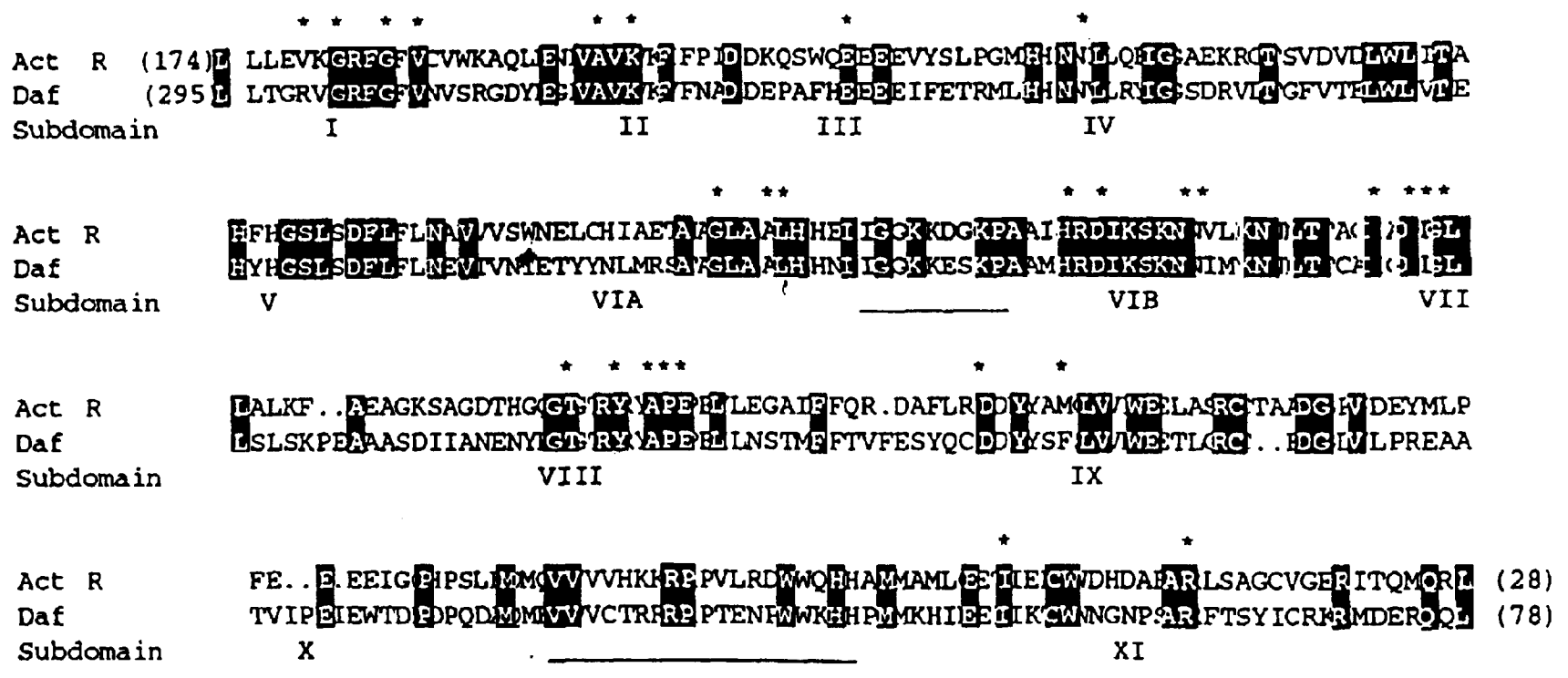

Comparision of the activin receptor sequence to the sequence databases revealed structural similarity in the intracellular domain to a number of receptor and non-receptor kinases. Analysis of the sequences of all kinases has led to the identification of a 300 amino acid kinase domain characterized by 12 subdomains containing a number of highly conserved amino acids [Hanks, S. K. and Quinn, A. M., Meth. Enzymol. 200:38–62 (1991) and Hanks et al., Science 241:42–52 (1988)]; the activin receptor sequence has all of these conserved subdomains in the proper order (FIG. 4). A conserved Gly in subdomain I is replaced by $Ala^{180}$ in the activin receptor, but this residue has also been observed in other kinases. Based upon structural relatedness, therefore, this receptor is expected to be a functional protein kinase.

The sequences in two of these subdomains (VIB and VIII) can be used to predict tyrosine vs. serine/threonine substrate specificity [Hanks et al., (1988) supra]. The sequence of the mouse activin receptor in both of these subdomains is characteristic of serine kinases.

TABLE 2

Kinase Domain Predictive Sequences

| Subdomain | VIB | SEQ ID NO. | VIII | SEQ ID NO. |
|---|---|---|---|---|
| serine kinase consensus | DLKPEN | 5 | G(T/S)XX(Y/F)X | 6 |
| activin receptor | DIKSKN | 7 | GTRRYM | 8 |
| tyrosine kinase consensus | DLAARN | 9 | XP(I/V) (K/R)W(T/M) | 10 |

Therefore, the activin receptor is expected to have serine/threonine specificity. Furthermore, the activin receptor does not have a tyrosine residue in the standard autophosphorylation region between subdomains VII and VIII, indicating that it is not a standard tyrosine kinase. The receptor could potentially autophosphorylate at $Ser^{333}$ or $Thr^{337}$. One interesting additional possibility is that the activin receptor kinase may have specificity for serine, threonine and tyrosine residues. Several kinases with these properties have recently been described (see, for example, Howell et al., Mol. Cell. Biol. 11:568–572 (1991), Stern et al., Mol. Cell. Biol. 11:987–1001 (1991) and Featherstond, C. and Russell, P., Nature 349:808–811 (1991)).

Figure 6:
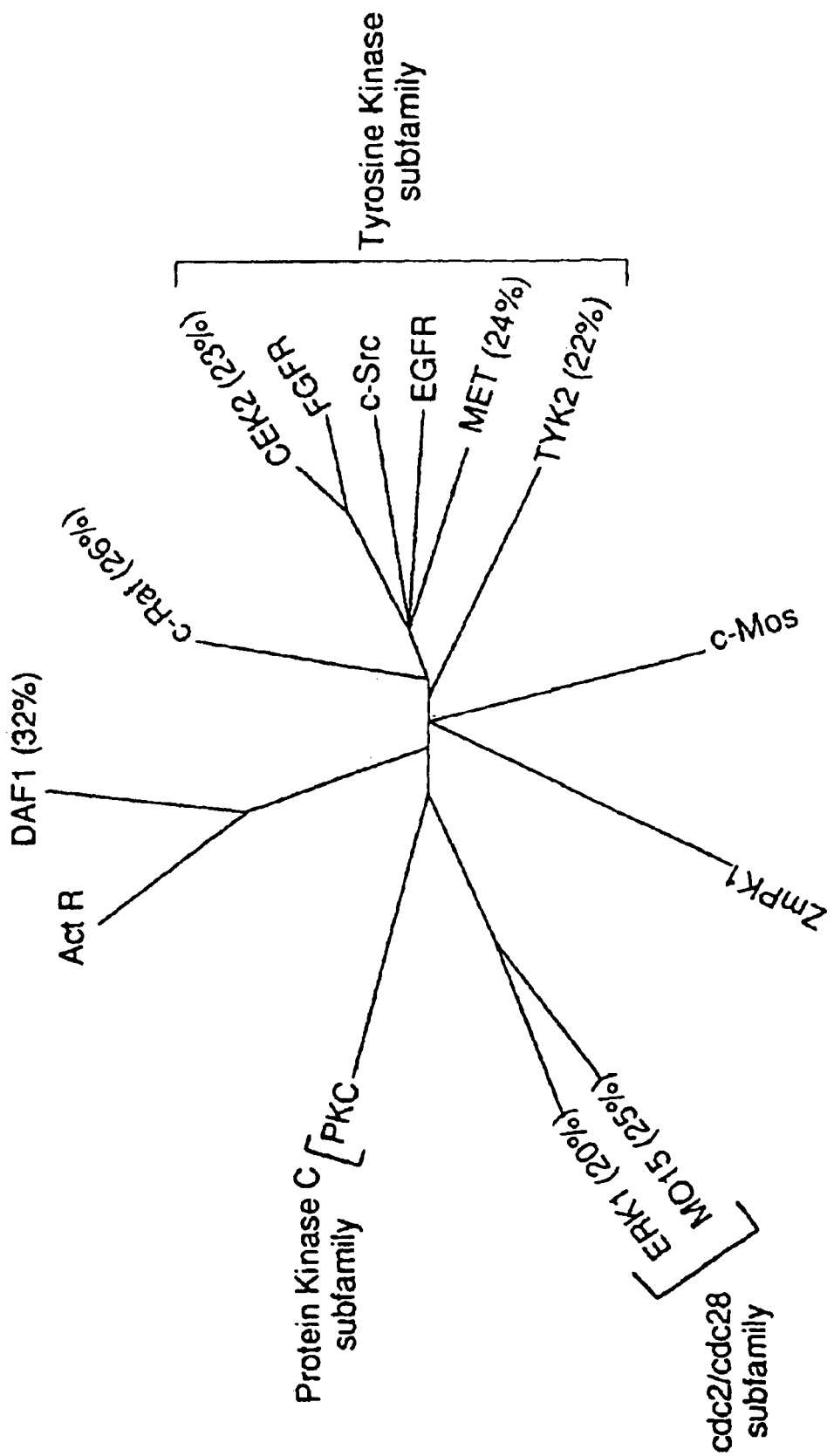
FIG. 6 is a phylogenetic tree, comparing the relationship of the activin receptor kinase domain to other protein kinases. To construct the tree, the catalytic domains of representative sequences were empirically aligned and evolutionary relatedness was calculated using an algorithm designed by Fitch and Margoliash [Science 155: 279–284 (1967)), as implemented by Feng and Doolittle [J. Mol. Evol. 25: 351–360 (1987)]. Known subfamilies of kinases are indicated in the figure. For those sequences that had similarity scores (i.e., a relative sequence identity) of at least 4 standard deviations above the mean (in comparison with all other known kinase sequences), the percent identity with the activin receptor is indicated. For further detail on kinase sequences, the reader is referred to Hanks and Quinn, Meth. Enzymol. 200: 38–62 (1991).

Phylogenetic analysis of the activin receptor compared to 161 other kinase sequences revealed that the activin receptor and the C.elegans protein, daf-1 [Georgi et al., Cell 61:635–645 (1990)] may constitute a separate subfamily of kinases (see FIG. 6). daf-1 is a putative transmembrane receptor involved in the developmental arrest of a non-feeding larval state and shares 32% identity with the activin receptor (see FIG. 6). Like the activin receptor, daf-1 is predicted to be a transmembrane serine/threonine-specific kinase; furthermore, both daf and the activin receptor have short, conserved inserts in the kinase domain sequence between subdomains VIA—VIB and X—XI that are not present in any other kinase (underlined in FIG. 4B). This additional similarity lends credence to their belonging to a unique subfamily of kinases. The activin receptor is quite distantly related (18% amino acid sequence identity) to the only other known transmembrane serine/threonine protein kinase, encloded by the ZmPK gene of maize [Walker, J. C. and Zhang, R., Nature 345:743–746 (1990)].

The extracellular domain of the activin receptor did not show similarity to any other sequences in the databases. This ligand binding domain is relatively small in comparison to those found in other growth factor receptors, but like those receptors this domain has a high cysteine content. The pattern of these Cys residues, however, is not like either an immunoglobulin fold or the cysteine rich repeats of the EGF receptor. There are also two potential sites of N-linked glycosylation in the extracellular domain, as well as a number of potential phosphorylation sites for protein kinase C and casein kinase II in the intracellular domain.

Example IX

Binding Properties of the Cloned Activin Receptor

To verify that the cloned receptor is activin specific, competition binding experiments were performed on COS cells transiently transfected with either pmActR1 or pmActR2. Cells transfected with either construct bound activin A with a single high affinity component (Kd=180 pM; FIG. 5), indicating that a functional (structurally complete) intracellular kinase domain is not required for ligand binding. This binding affinity is consistent with that measured on other activin-responsive cell types [see, for example, Campen, C. A. and Vale, W., Biochem. Biophys. Res. Comm. 157:844–849 (1988); Hino et al., J. Biol. Chem. 264:10309–10314 (1989); Sugino et al., J. Biol. Chem. 263: 15249–15252 (1988); and Kondo et al., Biochem. Biophys. Res. Comm, 161:1267–1272 (1989)]. Untransfected COS cells do not bind activin A. The transfected cultures as a whole expressed approximately 26,000 receptors per cell; however, because only 15% of the cells express the transfected gene (as measured by quantitating transfected cells as a fraction of all cells following dipping in emulsion), each transfected cell expressed an average of 175,000 receptors per cell. The level of expression per cell varies considerably, though, based on the number of accumulated silver grains. This value is comparable to the expression of other transfected cell surface proteins in COS cells.

Figure 5B:
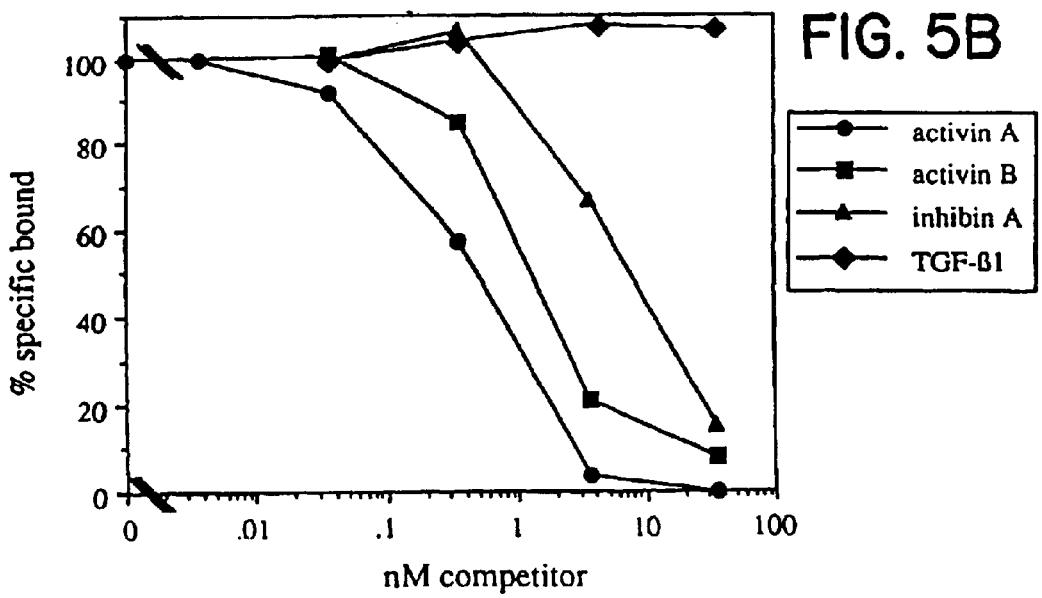
FIG. 5B summarizes results of $^{125}$I activin A binding to COS cells transfected with pmActR2. Binding was competed with unlabeled factors as indicated in the figure. For the runs reported herein, total binding was 3.4% of input cpm, non-specific binding was 0.9% of input cpm, and therefore the specific binding was 2.5% of input cpm. Data are shown as % specific binding, normalized to 100%.

Binding of iodinated activin A to COS cells transiently transfected with pmActR2 could be competed by activin B with slightly reduced potency compared to activin A; by inhibin A with approximately 10-fold lower potency; and could not be competed by TGF-β1 (FIG. 5B). This affinity and specificity of binding match those observed following binding of activin A to a number of other activin-responsive cell types. Although activin B appears to bind the transfected receptor with lower affinity than activin A, the activin B preparation used in these experiments may have suffered a reduction in potency, based on a comparison of bioactivity with activin A, since the recombinant synthesis of the activin B employed herein had been carried out some time ago (recombinant synthesis of activin B is described by Mason et al., in Mol. Endocrinol. 3: 1352–1358 (1989)). It is likely that this cDNA encodes a receptor for multiple forms of activin.

The size of the cloned activin receptor was analyzed by affinity cross-linking $^{125}$I activin A to COS cells transfected with pmActR2 using the bifunctional chemical cross-linker, disuccinimidyl suberate (DSS). A major cross-linked band of 84 kDa was observed in transfected, but not in untransfected cells. Subtracting the molecular weight of activin, this represents a protein of 56 kDa, which corresponds well to the molecular weight predicted from the nucleic acid sequence data. Cross-linking $^{125}$I activin A to AtT20 cells yields a major band of 65 kDa, with minor bands of approximately 78 and 84 kDa. The size of the largest band matches that generated by the cloned receptor. The smaller bands could be either separate proteins, different phosphorylated forms of the same protein, or degradation products of the full length clone; the sequences DKKRR at amino acid 35 and KKKR at amino acid 416 could be potential sites of proteolysis. Alternatively, these bands could come from alternatively spliced products of the same gene.

The 84 and 65 kDa cross-linked bands have also been observed in other activin-responsive cell types [Hino, supra; Centrella et al., Mol. Cell. Biol. 11:250–258 (1991)], and interpreted to represent the signalling receptor, although complexes of other sizes have also been seen as well. The size of the activin receptor is very similar to a putative TGF-β receptor, to the limited extent it has been characterized by chemical cross-linking [see Massague et al., Ann. N.Y. Acad. Sci. 593: 59–72 (1990)].

Example X

Expression of Activin Receptor mRNA

The distribution of activin receptor mRNA was analyzed by Northern blot. Two mRNA species, of 6.0 and 3.0 kb, were observed in AtT20 cells as well as a number of mouse tissues, including brain, testis, pancreas, liver and kidney. The total combined size of the inserts from pmActR1 and pmActR2 is 3.1 kb, which corresponds to the size of the smaller transcript. Neither the extent of similarity between the two mRNAs, nor the significance of having two transcripts is clear. The genes for several other hormone receptors have been shown to be alternatively spliced to generate both a cell surface receptor and a soluble binding protein, and it is possible that the activin receptor is processed in a similar manner.

Interestingly, the relative abundance of the two transcripts varies depending on the source. While AtT20 cells have approximately equal levels of both mRNAs, most tissues had much greater levels of the 6.0 kb transcript, with little or no expression of the 3.0 kb transcript. Testis, on the other hand, had a greater amount of the 3.0 kb band. Expression of activin receptor mRNA in brain, liver and testis is in accord with described biological actions of activin in those tissues [Mine et al., Endocrinol. 125:586–591 (1989); Vale et al., Peptide Growth Factors and Their Receptors, Handbook of Experimental Pharmacology, M. A. Sporn and A. B. Roberts, ed., Springer-Verlag (1990), in press].

Example XI

Identification of a Human Activin Receptor

A human testis library (purchased from Clontech; catalog no. HL1010b) was probed with the full length mouse activin receptor gene (see Sequence ID No. 1) under the following conditions:

Hybridization stringency:
20% formamide, 6×SSC at 42° C.;
Wash stringency:
2×SSC, 0.1% SDS at 42° C.

A sequence which is highly homologous with the mouse activin receptor was identified (Sequence ID No. 15). Due to the high degree of homology between this receptor and the mouse activin receptor, this receptor is designated as the human form of the activin receptor from the same subclass as the mouse receptor described above.

Example XII

Identification of a Xenopus Activin Receptor

A Xenopus stage 17 embryo cDNA library (prepared as described by Kintner and Melton in Development 99: 311–325 (1987) was probed with the full length mouse activin receptor gene (see Sequence ID No. 1) under the following conditions:

Hybridization stringency:
20% formamide, 6×SSC at 42° C.;
Wash stringency:
2×SSC, 0.1% SDS at 42° C.

A sequence having a substantial degree of homology with respect to the mouse activin receptor was identified (Sequence ID No. 3). The degree of overall amino acid homology (relative to the mouse acitvin receptor) is only about 69% (with 77% homology in the intracellular domain and 58% homology in the extracellular domain). Due to the moderate degree of homology between this receptor and the mouse activin receptor, this receptor is designated as an activin receptor from a different subclass than the mouse receptor described above.

Example XIII

Functional Assays of ActRs in Xenopus Embryos

To determine whether xActRIIB can transmit a signal in response to activin, xActRIIB RNA was synthesized in vitro and injected into Xenopus embryos at two different concentrations. Injected embryos were allowed to develop to stage 9, at which time animal caps were dissected and treated overnight with different concentrations of activin. The xActRIIB cDNA was cloned into rp64T [see Krieg and Melton in Methods in Enzymology, Abelson and Simon, Eds. (Academic Press, New York, 1987), vol. 155, p. 397] and transcribed in vitro to generate a capped, synthetic xActRIIB RNA [see Melton et al., in Nucleic Acids Res. 12:7035 (1984) and Kintner in Neuron 1:545 (1988)]. Embryos at the two- to four-cell stage were injected with about 20 nl of RNA at concentrations of 0.02 ng/nl, or 0.1 ng/nl, spread between four quadrants of the animal pole. At stage 9, animal caps were removed from RNA-injected embryos and incubated in 0.5× modified mammalian Ringer's (MMR), 0.1% bovine serum albumin (BSA) with different concentrations of purified, porcine activin A (six caps per incubation). After 20 hours in culture, total RNA was prepared.

The response of the caps to activin was assessed by quantifying muscle-specific actin RNA with a ribonuclease protection assay as per Blackwell and Weintraub, Science 250:1104 (1990). Embryos injected with 0.4 and 2.0 ng of xActRIIB RNA were approximately 10- and 100-fold more sensitive, respectively, to activin than control embryos. The low amount of muscle actin found in animal caps in the absence of added activin A is probably a consequence of contamination of the animal cap with a small amount of marginal zone tissue.

The amount of muscle actin decreased with increasing concentration of activin in the embryos injected with 2 ng of xActRIIB RNA. This is consistent with the observation that isolated animal cap cells uniformly exposed to different concentrations of activin only form muscle cells in response to a narrow range of activin concentrations [see Blackmann and Kadesch in Genes and Development 5:1057 (1990)]. The present results indicate that the concentration of ligand and the amount of receptor are both important in determining the signal transmitted. Thus, the range of activin concentrations that lead to muscle differentiation is lower in animal cap cells from injected embryos, which are expressing more receptor than normal, than from uninjected embryos.

Example XIV

Analysis of Kinase Activity of mActRII

A fragment of cDNA corresponding to the entire intracellular domain of mActRII (amino acids 143–494) was subcloned into the vector pGEX-2T [see Smith and Johnson in Gene 67:31–40 (1988)], creating a fusion protein between glutathione S-transferase (GST) and the putative kinase domain of the receptor. This plasmid was introduced into bacteria and the expressed fusion protein was purified using glutathione affinity chromatography as described by Smith and Johnson. Approximately 100–200 ng of fusion protein, or of purified GST, were incubated with 25 $\mu$Ci [$\gamma$-$^{32}$P] ATP in a buffer containing 50 mM Tris, 10 mM MgCl$_2$ for 30 minutes at 37° C. The products were analyzed by SDS-PAGE and autoradiography. The fusion protein, but not the GST alone, became phosphorylated, indicating that the kinase domain of the fusion protein was functional. Phosphoamino acid analysis, performed according to Cooper et al. [Meth. Enzym. 99:387 (1983)], indicated that the predominant amino acid residue that became phosphorylated was threonine.

Example XV

Identification of a Rat Activin Receptor

Degenerate primers deduced from the conserved serine/threonine kinase domains of activin/TGFβ type II receptors were used to perform reverse-transcription polymerase chain reaction (RT-PCR) on a rat cDNA library derived from adult rat pituitary or brain. A mixture of oligo (dT)-primed cDNAs from 5 $\mu$g of total RNA were used as templates for PCR. The degenerate primers used were:

H1: 5'-CGGGATCCGTNGCNGTNAARATHTTYCC-3' (SEQ ID NO:13) (a sense primer corresponding to amino acid sequence 216–221 of SEQ ID NO:1 in kinase subdomain II); and H 3 : 5'-CGGGATCCYTCNGGNGCCATRTANCKYCTNGTNCC-3' (SEQ ID NO:14) (an antisense primer corresponding to amino acid sequence 361–369 of SEQ ID NO:1 in the kinase subdomain VIII).

The primers have BamHI sites at the 5' termini to facilitate the subcloning of the resulting PCR products. The PCR reaction included an initial denaturation step at 94° C. for 5 min, 35 cycles of 94° C. for 1 min, 46° C. for 2 min, and 72° C. for 3 min, and a final incubation for 10 min at 72° C. The PCR products were purified and subcloned into the pBluescript vector (Stratagene, La Jolla, Calif.) and sequenced.

Four fragments having serine/threonine kinase motifs were isolated. Among them, three were previously characterized as ActRI (ALK2), ActRIB (ALK4) and TSRI (ALK1). A full length cDNA of a fourth novel clone from an adult rat brain cDNA library was isolated, and tentatively named ALK7 (activin receptor-like kinase 7). The nucleotide and amino acid sequences for ALK7 are set forth in SEQ ID NOs:11 and 12.

The kinase domain of ALK7 shows highest sequence similarity to that of ActRIB and TGFβRI (82.50% identities with them), and the entire amino acid sequence shows 64.0% identity to that of TGFβRI, and 62.1 identity to that of ActRIB. Furthermore, ALK7 has a "GS domain" almost identical to TGFβRI and ActRIB, and contains cystein residues in the extracellular ligand binding domain conserved among the receptor serine kinase superfamily. This indicates that ALK7 may function as a type I receptor for the TGF-β superfamily.

RNase protection assays using RNAs isolated from various rat brain, kidney, stomach, spleen, heart, skin, skeletal muscle, ovary and testis were conducted to determine the expression patterns of the ALK7 gene. Although ALK7 mRNA is not expressed at a high level in adult tissues, it is clearly detectable in brain and to a lesser extent in kidney and ovary.

Functional characterization of ALK7 or an ALK7 mutant ALK7(T194D)) was performed in the mink lung cell-line "RlB", Chinese Hamster Ovary cell-line (CHO), and human myelogenous leukemia cell (K562). These cells were transfected with ALK7 or an ALK7(T194D) along with the transcriptional reporter construct (3TP-Lux). The mutant (ALK7(T194D)) has an aspartate residue at position 194 in the "GS domain" instead of threonine. The plasmid p3TP-Lux, which contains three copies of a TPA-responsive element and the promoter of the human plasminogen activator inhibitor-1 (PAI-1) linked to the luciferase reporter gene, has been shown to be responsive to TGFβ or activin (see, e.g. Carcamo et al., 1994, Molec. Cell Biol., 14:3810–3821). After 24 hours of transfection, cells were cultured in medium containing 0.2–0.5% serum with or without ligands for 12–24 hours, and the luciferase avtivity of cell lysates was measured. Although the physiological ligand that activates ALK7 has yet to be determined, ALK7 (T194D) activates the transcriptional response at a level approximately 3–4 fold higher than the wild type protein, indicating that the mutant is constitutively active.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of a cDNA encoding a mouse-derived activin receptor of the present invention.

Sequence ID No. 15 is a nucleic acid sequence encoding a human-derived activin receptor of the present invention. Sequence ID No. 15 is substantially the same as Sequence ID No. 1, except that the codon for amino acid residue number 39 encodes lysine (i.e., nucleotides 185–187 are AAA or AAG), the codon for amino acid residue 92 encodes valine (i.e., nucleotides 344–346 are GTN, wherein N is A, C, G or T), and the codon for amino acid residue number 288 encodes glutamine (i.e., nucleotides 932–934 are CAA or CAG).

Sequence ID No. 2 is the deduced amino acid sequence of a mouse-derived activin receptor of the present invention.

Sequence ID No. 16 is an amino acid sequence for a human-derived activin receptor of the present invention. Sequence ID No. 16 is substantially the same as Sequence ID No. 2, except that amino acid residue number 39 is lysine, amino acid residue 92 is valine, and amino acid residue number 288 is glutamine.

Sequence ID No. 3 is the nucleic acid sequence (and the deduced amino acid sequence) of a cDNA encoding a Xenopus-derived activin receptor of the present invention.

Sequence ID No. 4 is the deduced amino acid sequence of a Xenopus-derived activin receptor of the present invention.

Sequence ID No. 5 is the amino acid sequence of the VIB subdomain of the serine kinase consensus sequence.

Sequence ID No. 6 is the amino acid sequence of the VIII subdomain of the serine kinase consensus sequence.

Sequence ID No. 7 is the amino acid sequence of the VIB subdomain of the invention activin receptor.

Sequence ID No. 8 is the amino acid sequence of the VIII subdomain of the invention activin receptor.

Sequence ID No. 9 is the amino acid sequence of the VIB subdomain of the tyrosine kinase consensus sequence.

Sequence ID No. 10 is the amino acid sequence of the VIII subdomain of the tyrosine kinase consensus sequence.

Sequence ID No. 11 is the nucleic acid sequence (and the deduced amino acid sequence) of a cDNA encoding rat-derived activin receptor of the present invention.

Sequence ID No. 12 is the deduced amino acid sequence of a rat-derived activin receptor of the present invention.

Sequence ID No. 13 is the Hi degenerate primer employed in Example XV.

Sequence ID No. 14 is the H3 degenerate primer employed in Example XV.

That which is claimed is:

1. A method for screening a collection of compounds to determine those compounds which bind to at least one member of the activin/TGF-β receptor superfamily, said method comprising employing a vertebrate activin receptor member of the activin/TGF-β receptor superfamily in a competitive binding assay, wherein said vertebrate activin receptor has binding affinity for activin and has at least 80% amino acid identity with amino acid residues 20–513 of SEQ ID NO:16; and is;

wherein the receptor is further characterized by having the following domains, reading from the N-terminal end of said protein:

an extracellular, ligand-binding domain, a hydrophobic, trans-membrane domain, and an intracellular serine/threonine kinase domain.

2. A method according to claim 1, wherein said receptor has at least 90% amino acid identity with amino acid residues 20–513 of SEQ ID NO.16.

3. A method according to claim 1, wherein said receptor comprises the amino acid sequence of residues 20–513 as set forth in SEQ ID NO.16.

4. A method according to claim 3, wherein said receptor further comprises the amino acid sequence of residues 1–19 as set forth in SEQ ID NO.16.

5. A method for screening a collection of compounds to determine those compounds which bind to at least one member of the activin/TGF-β receptor superfamily, said method comprising employing a soluble polypeptide domain of a member of the activin/TGF-β receptor superfamily in a competitive binding assay, wherein said soluble polypeptide has binding affinity for activin and has at least 80% amino acid identity with amino acid residues 20–134 of SEQ ID NO.16.

6. A method according to claim 5, wherein said polypeptide has at least 90% amino acid identity with amino acid residues 20–134 of SEQ ID NO.16.

7. A method according to claim 5, wherein said receptor comprises the amino acid sequence of residues 20–134 as set forth in SEQ ID NO.16.

8. A method according to claim 7, wherein said receptor further comprises the amino acid sequence of residues 1–19 as set forth in SEQ ID NO.16.

9. A method for screening a collection of compounds to determine those compounds which bind to at least one member of the activin/TGF-β superfamily, said method comprising employing a vertebrate activin receptor in a competitive binding assay, wherein said vertebrate activin receptor has binding affinity for activin and is encoded by nucleotides having at least 90% sequence homology with respect to the contiguous nucleotide sequence of nucleotides 128–1609 of SEQ ID NO.15.

10. A method according to claim 9, wherein the contiguous nucleotide sequence further comprises nucleotides 71–127 of SEQ ID NO.15.

* * * * *

UNITED STATES PATENT AND TRADEMARK OFFICE
CERTIFICATE OF CORRECTION

PATENT NO. : 6,835,544 B2  Page 1 of 1
DATED : December 28, 2004
INVENTOR(S) : Mathews et al.

It is certified that error appears in the above-identified patent and that said Letters Patent is hereby corrected as shown below:

<u>Title page,</u>
Item [*] Notice, delete "by 105 days" and insert -- by 375 days --.

Signed and Sealed this

Twenty-fifth Day of April, 2006

JON W. DUDAS
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 2563 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 71..1609

(xi) SEQUENCE DESCRIPTION: SEQ ID NO: 1:

```
CTCCGAGGAA GACCCAGGGA ACTGGATATC TAGCGAGAAC TTCCTACGGC TTCTCCGGCG        60

CCTCGGGAAA ATG GGA GCT GCT GCA AAG TTG GCG TTC GCC GTC TTT CTT         109
            Met Gly Ala Ala Ala Lys Leu Ala Phe Ala Val Phe Leu
              1               5                  10

ATC TCT TGC TCT TCA GGT GCT ATA CTT GGC AGA TCA GAA ACT CAG GAG         157
Ile Ser Cys Ser Ser Gly Ala Ile Leu Gly Arg Ser Glu Thr Gln Glu
     15                  20                  25

TGT CTT TTC TTT AAT GCT AAT TGG GAA AGA GAC AGA ACC AAC CAG ACT         205
Cys Leu Phe Phe Asn Ala Asn Trp Glu Arg Asp Arg Thr Asn Gln Thr
 30                  35                  40                  45

GGT GTT GAA CCT TGC TAT GGT GAT AAA GAT AAA CGG CGA CAT TGT TTT         253
Gly Val Glu Pro Cys Tyr Gly Asp Lys Asp Lys Arg Arg His Cys Phe
                 50                  55                  60

GCT ACC TGG AAG AAT ATT TCT GGT TCC ATT GAA ATA GTG AAG CAA GGT         301
Ala Thr Trp Lys Asn Ile Ser Gly Ser Ile Glu Ile Val Lys Gln Gly
             65                  70                  75

TGT TGG CTG GAT GAT ATC AAC TGC TAT GAC AGG ACT GAT TGT ATA GAA         349
Cys Trp Leu Asp Asp Ile Asn Cys Tyr Asp Arg Thr Asp Cys Ile Glu
         80                  85                  90

AAA AAA GAC AGC CCT GAA GTG TAC TTT TGT TGC TGT GAG GGC AAT ATG         397
Lys Lys Asp Ser Pro Glu Val Tyr Phe Cys Cys Cys Glu Gly Asn Met
     95                 100                 105

TGT AAT GAA AAG TTC TCT TAT TTT CCG GAG ATG GAA GTC ACA CAG CCC         445
```

```
Cys Asn Glu Lys Phe Ser Tyr Phe Pro Glu Met Glu Val Thr Gln Pro
110             115                 120                 125

ACT TCA AAT CCT GTT ACA CCG AAG CCA CCC TAT TAC AAC ATT CTG CTG          493
Thr Ser Asn Pro Val Thr Pro Lys Pro Pro Tyr Tyr Asn Ile Leu Leu
            130                 135                 140

TAT TCC TTG GTA CCA CTA ATG TTA ATT GCA GGA ATT GTC ATT TGT GCA          541
Tyr Ser Leu Val Pro Leu Met Leu Ile Ala Gly Ile Val Ile Cys Ala
                145                 150                 155

TTT TGG GTG TAC AGA CAT CAC AAG ATG GCC TAC CCT CCT GTA CTT GTT          589
Phe Trp Val Tyr Arg His His Lys Met Ala Tyr Pro Pro Val Leu Val
            160                 165                 170

CCT ACT CAA GAC CCA GGA CCA CCC CCA CCT TCC CCA TTA CTA GGG TTG          637
Pro Thr Gln Asp Pro Gly Pro Pro Pro Pro Ser Pro Leu Leu Gly Leu
    175                 180                 185

AAG CCA TTG CAG CTG TTA GAA GTG AAA GCA AGG GGA AGA TTT GGT TGT          685
Lys Pro Leu Gln Leu Leu Glu Val Lys Ala Arg Gly Arg Phe Gly Cys
190                 195                 200                 205

GTC TGG AAA GCC CAG TTG CTC AAT GAA TAT GTG GCT GTC AAA ATA TTT          733
Val Trp Lys Ala Gln Leu Leu Asn Glu Tyr Val Ala Val Lys Ile Phe
                210                 215                 220

CCA ATA CAG GAC AAA CAG TCC TGG CAG AAT GAA TAT GAA GTC TAT AGT          781
Pro Ile Gln Asp Lys Gln Ser Trp Gln Asn Glu Tyr Glu Val Tyr Ser
            225                 230                 235

CTA CCT GGA ATG AAG CAT GAG AAC ATA CTA CAG TTC ATT GGT GCA GAG          829
Leu Pro Gly Met Lys His Glu Asn Ile Leu Gln Phe Ile Gly Ala Glu
        240                 245                 250

AAA AGA GGC ACC AGT GTG GAT GTG GAC CTG TGG CTA ATC ACA GCA TTT          877
Lys Arg Gly Thr Ser Val Asp Val Asp Leu Trp Leu Ile Thr Ala Phe
255                 260                 265

CAT GAA AAG GGC TCA CTG TCA GAC TTT CTT AAG GCT AAT GTG GTC TCT          925
His Glu Lys Gly Ser Leu Ser Asp Phe Leu Lys Ala Asn Val Val Ser
270                 275                 280                 285

TGG AAT GAA CTT TGT CAT ATT GCA GAA ACC ATG GCT AGA GGA TTG GCA          973
Trp Asn Glu Leu Cys His Ile Ala Glu Thr Met Ala Arg Gly Leu Ala
                290                 295                 300

TAT TTA CAT GAG GAT ATA CCT GGC TTA AAA GAT GGC CAC AAG CCT GCA         1021
Tyr Leu His Glu Asp Ile Pro Gly Leu Lys Asp Gly His Lys Pro Ala
            305                 310                 315

ATC TCT CAC AGG GAC ATC AAA AGT AAA AAT GTG CTG TTG AAA AAC AAT         1069
Ile Ser His Arg Asp Ile Lys Ser Lys Asn Val Leu Leu Lys Asn Asn
        320                 325                 330

CTG ACA GCT TGC ATT GCT GAC TTT GGG TTG GCC TTA AAG TTC GAG GCT         1117
Leu Thr Ala Cys Ile Ala Asp Phe Gly Leu Ala Leu Lys Phe Glu Ala
    335                 340                 345

GGC AAG TCT GCA GGT GAC ACC CAT GGG CAG GTT GGT ACC CGG AGG TAT         1165
Gly Lys Ser Ala Gly Asp Thr His Gly Gln Val Gly Thr Arg Arg Tyr
350                 355                 360                 365

ATG GCT CCA GAG GTG TTG GAG GGT GCT ATA AAC TTC CAA AGG GAC GCA         1213
Met Ala Pro Glu Val Leu Glu Gly Ala Ile Asn Phe Gln Arg Asp Ala
                370                 375                 380

TTT CTG AGG ATA GAT ATG TAC GCC ATG GGA TTA GTC CTA TGG GAA TTG         1261
Phe Leu Arg Ile Asp Met Tyr Ala Met Gly Leu Val Leu Trp Glu Leu
            385                 390                 395

GCT TCT CGT TGC ACT GCT GCA GAT GGA CCC GTA GAT GAG TAC ATG TTA         1309
Ala Ser Arg Cys Thr Ala Ala Asp Gly Pro Val Asp Glu Tyr Met Leu
        400                 405                 410

CCA TTT GAG GAA GAA ATT GGC CAG CAT CCA TCT CTT GAA GAT ATG CAG         1357
Pro Phe Glu Glu Glu Ile Gly Gln His Pro Ser Leu Glu Asp Met Gln
415                 420                 425
```

```
GAA GTT GTT GTG CAT AAA AAA AAG AGG CCT GTT TTA AGA GAT TAT TGG      1405
Glu Val Val Val His Lys Lys Lys Arg Pro Val Leu Arg Asp Tyr Trp
430                 435                 440                 445

CAG AAA CAT GCA GGA ATG GCA ATG CTC TGT GAA ACG ATA GAA GAA TGT      1453
Gln Lys His Ala Gly Met Ala Met Leu Cys Glu Thr Ile Glu Glu Cys
                450                 455                 460

TGG GAT CAT GAT GCA GAA GCC AGG TTA TCA GCT GGA TGT GTA GGT GAA      1501
Trp Asp His Asp Ala Glu Ala Arg Leu Ser Ala Gly Cys Val Gly Glu
            465                 470                 475

AGA ATT ACT CAG ATG CAA AGA CTA ACA AAT ATC ATT ACT ACA GAG GAC      1549
Arg Ile Thr Gln Met Gln Arg Leu Thr Asn Ile Ile Thr Thr Glu Asp
        480                 485                 490

ATT GTA ACA GTG GTC ACA ATG GTG ACA AAT GTT GAC TTT CCT CCC AAA      1597
Ile Val Thr Val Val Thr Met Val Thr Asn Val Asp Phe Pro Pro Lys
    495                 500                 505

GAA TCT AGT CTA TGATGGTGGC ACCGTCTGTA CACACTGAGG ACTGGGACTC          1649
Glu Ser Ser Leu
510

TGAACTGGAG CTGCTAAGCT AAGGAAAGTG CTTAGTTGAT TTTCTGTGTG AAATGAGTAG    1709

GATGCCTCCA GGACATGTAC GCAAGCAGCC CCTTGTGGAA AGCATGGATC TGGGAGATGG    1769

ATCTGGGAAA CTTACTGCAT CGTCTGCAGC ACAGATATGA AGAGGAGTCT AAGGGAAAAG    1829

CTGCAAACTG TAAAGAACTT CTGAAAATGT ACTCGAAGAA TGTGGCCCTC TCCAAATCAA    1889

GGATCTTTTG GACCTGGCTA ATCAAGTATT TGCAAAACTG ACATCAGATT TCTTAATGTC    1949

TGTCAGAAGA CACTAATTCC TTAAATGAAC TACTGCTATT TTTTTAAAT GAAAAACTTT     2009

TCATTTCAGA TTTTAAAAAG GGTAACTTTT TATTGCATTT GCTGTTGTTT CTATAAATGA    2069

CTATTGTAAT GCCAACATGA CACAGCTTGT GAATGTGTAG TGTGCTGCTG TTCTGTGTAC    2129

ATAGTCATCA AAGTGGGGTA CAGTAAAGAG GCTTCCAAGC ATTACTTTAA CCTCCCTCAA    2189

CAAGGTATAC CTCAGTTCCA CGGTTGTTAA ATTATAAAAT TGAAACACT AACAGAATTT     2249

GAATAAATCA GTCCATGTTT TATAACAAGG TTAATTACAA ATTCACTGTG TTATTTAAGA    2309

AAAAATGGTA AGCTATGCTT AGTGCCAATA GTAAGTGGCT ATTTGTAAAG CAGTGTTTTA    2369

GCTTTTCTTC TACTGGCTTG TAATTTAGGG AAAACAAGTG CTGTCTTTGA AATGGAAAAG    2429

AATATGGTGT CACCCTACCC CCCATACTTA TATCAAGGTC CCAAAATATT CTTTTCCATT    2489

TCAAAGACAG CACTTTGAAA ACCCTAAATT ACAAGCCAGT AGAAGAAAAG CTAAAACACG    2549

CTTTACAAAT AGCC                                                      2563

(2) INFORMATION FOR SEQ ID NO: 2:

(i) SEQUENCE CHARACTERISTICS:
        (A) LENGTH: 513 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Arg Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60
```

-continued

```
Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Ile Glu Lys Lys Asp
                 85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
        130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
        210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
        290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
        450                 455                 460

Asp Ala Glu Ala Arg Leu Ser Ala Gly Cys Val Gly Glu Arg Ile Thr
465                 470                 475                 480
```

-continued

```
Gln Met Gln Arg Leu Thr Asn Ile Ile Thr Thr Glu Asp Ile Val Thr
                485                 490                 495
Val Val Thr Met Val Thr Asn Val Asp Phe Pro Pro Lys Glu Ser Ser
            500                 505                 510
Leu
```

(2) INFORMATION FOR SEQ ID NO: 3:

(i) SEQUENCE CHARACTERISTICS:
        (A) LENGTH: 2335 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: XACTR (ix) FEATURE:
        (A) NAME/KEY: CDS
        (B) LOCATION: 468..1997

(xi) SEQUENCE DESCRIPTION: SEQ ID NO: 3:

```
CCGCCCACAC AGTGCAGTGA ATAATAGCCG GTGCGGCCCC TCCCCTCTTT CCCTGGCAGT      60

TGTGTATCTG TCACATTGAA GTTTGGGCTC CTGTGAGTCT GAGCCTCCCC CTGTGTCTCA     120

TGTGAAGCTG CTGCTGCAGA AGGTGGAGTC GTTGCATGAG GGTGGGGGGA GTCGCTGCTG     180

TTTGATCTGC CTCTGCTCCC CATTCACACT CTCATTTCAT TCCCACGGAT CCACATTACA     240

ACTCGCCTTT AACCCTTTCC CTGGCGGAGC CCACGCGTCT TTCATCCCTC CTGCCGCGGC     300

CGCTGAGCGA CCAGAGCGCG ACATTGTTGC GGCGGGGGAT TGGGCGACAT TGTTGCGAAT     360

AATCGGAGCT GCTGGGGGGG AACTGATACA ACGTTGCGAC TGTAAAGGAA TTAACTCGGC     420

CGAATGGGAT TTTATCTGTG TCGGTGAGAG AAGCGGATCC CAGGAGC ATG GGG GCG      476
                                                   Met Gly Ala
                                                     1

TCT GTA GCG CTG ACT TTT CTA CTT CTT CTT GCA ACT TTC CGC GCA GGC      524
Ser Val Ala Leu Thr Phe Leu Leu Leu Leu Ala Thr Phe Arg Ala Gly
    5                  10                  15

TCA GGA CAC GAT GAA GTG GAG ACA AGA GAG TGC ATC TAT TAC AAT GCC      572
Ser Gly His Asp Glu Val Glu Thr Arg Glu Cys Ile Tyr Tyr Asn Ala
 20                  25                  30                  35

AAC TGG GAA CTG GAG AAG ACC AAC CAA AGT GGG GTG GAA AGC TGC GAA      620
Asn Trp Glu Leu Glu Lys Thr Asn Gln Ser Gly Val Glu Ser Cys Glu
                 40                  45                  50

GGG GAA AAG GAC AAG CGA CTC CAC TGT TAC GCG TCT TGG AGG AAC AAT      668
Gly Glu Lys Asp Lys Arg Leu His Cys Tyr Ala Ser Trp Arg Asn Asn
             55                  60                  65

TCG GGC TTC ATA GAG CTG GTG AAA AAA GGA TGC TGG CTG GAT GAC TTC      716
Ser Gly Phe Ile Glu Leu Val Lys Lys Gly Cys Trp Leu Asp Asp Phe
         70                  75                  80

AAC TGT TAT GAC AGA CAG GAA TGT ATT GCC AAG GAA GAA AAC CCC CAA      764
Asn Cys Tyr Asp Arg Gln Glu Cys Ile Ala Lys Glu Glu Asn Pro Gln
     85                  90                  95

GTC TTT TTC TGC TGC TGC GAG GGA AAC TAC TGC AAC AAG AAA TTT ACT      812
Val Phe Phe Cys Cys Cys Glu Gly Asn Tyr Cys Asn Lys Lys Phe Thr
100                 105                 110                 115

CAT TTG CCT GAA GTC GAA ACA TTT GAT CCG AAG CCC CAG CCG TCA GCC      860
His Leu Pro Glu Val Glu Thr Phe Asp Pro Lys Pro Gln Pro Ser Ala
                120                 125                 130

TCC GTA CTG AAC ATT CTG ATC TAT TCC CTG CTT CCA ATT GTT GGT CTT      908
```

-continued

|  |  |
|---|---|
| Ser Val Leu Asn Ile Leu Ile Tyr Ser Leu Leu Pro Ile Val Gly Leu<br>                135                   140               145 |  |
| TCC ATG GCA ATT CTC CTG GCG TTC TGG ATG TAC CGT CAT CGA AAG CCT<br>Ser Met Ala Ile Leu Leu Ala Phe Trp Met Tyr Arg His Arg Lys Pro<br>         150                    155                 160 | 956 |
| CCC TAC GGG CAT GTA GAG ATC AAT GAG GAC CCC GGT CTG CCC CCT CCA<br>Pro Tyr Gly His Val Glu Ile Asn Glu Asp Pro Gly Leu Pro Pro Pro<br>         165                    170                 175 | 1004 |
| TCT CCT CTG GTC GGG CTG AAG CCG CTG CAG TTG CTG GAG ATA AAG GCG<br>Ser Pro Leu Val Gly Leu Lys Pro Leu Gln Leu Leu Glu Ile Lys Ala<br>180                   185                   190               195 | 1052 |
| CGA GGC CGT TTC GGT TGC GTC TGG AAA GCT CGT CTG CTG AAT GAA TAT<br>Arg Gly Arg Phe Gly Cys Val Trp Lys Ala Arg Leu Leu Asn Glu Tyr<br>                  200                   205               210 | 1100 |
| GTC GCA GTG AAA ATC TTC CCC GTG CAG GAT AAG CAG TCG TGG CAG TGT<br>Val Ala Val Lys Ile Phe Pro Val Gln Asp Lys Gln Ser Trp Gln Cys<br>                  215                   220               225 | 1148 |
| GAG AAA GAG ATC TTC ACC ACG CCG GGC ATG AAA CAT GAA AAC CTA TTG<br>Glu Lys Glu Ile Phe Thr Thr Pro Gly Met Lys His Glu Asn Leu Leu<br>         230                    235                 240 | 1196 |
| GAG TTC ATT GCC GCT GAG AAG AGG GGA AGC AAC CTG GAG ATG GAG CTG<br>Glu Phe Ile Ala Ala Glu Lys Arg Gly Ser Asn Leu Glu Met Glu Leu<br>         245                    250                 255 | 1244 |
| TGG CTC ATC ACT GCA TTT CAT GAT AAG GGT TCT CTG ACG GAC TAC CTG<br>Trp Leu Ile Thr Ala Phe His Asp Lys Gly Ser Leu Thr Asp Tyr Leu<br>260                   265                   270               275 | 1292 |
| AAA GGG AAC TTG GTG AGC TGG AAT GAA CTG TGT CAC ATA ACA GAA ACA<br>Lys Gly Asn Leu Val Ser Trp Asn Glu Leu Cys His Ile Thr Glu Thr<br>                  280                   285               290 | 1340 |
| ATG GCT CGT GGG CTG GCC TAC TTA CAT GAA GAT GTG CCC CGC TGT AAA<br>Met Ala Arg Gly Leu Ala Tyr Leu His Glu Asp Val Pro Arg Cys Lys<br>                  295                   300               305 | 1388 |
| GGT GAA GGG CAC AAA CCT GCA ATC GCT CAC AGA GAT TTT AAA AGT AAG<br>Gly Glu Gly His Lys Pro Ala Ile Ala His Arg Asp Phe Lys Ser Lys<br>         310                    315                 320 | 1436 |
| AAT GTA TTG CTA AGA AAC GAC CTG ACT GCG ATA TTA GCA GAC TTC GGG<br>Asn Val Leu Leu Arg Asn Asp Leu Thr Ala Ile Leu Ala Asp Phe Gly<br>         325                    330                 335 | 1484 |
| CTG GCC GTA CGA TTT GAG CCT GGA AAA CCT CCG GGA GAT ACA CAC GGG<br>Leu Ala Val Arg Phe Glu Pro Gly Lys Pro Pro Gly Asp Thr His Gly<br>340                   345                   350               355 | 1532 |
| CAG GTT GGC ACC AGG AGG TAT ATG GCT CCT GAG GTT CTA GAG GGA GCA<br>Gln Val Gly Thr Arg Arg Tyr Met Ala Pro Glu Val Leu Glu Gly Ala<br>                  360                   365               370 | 1580 |
| ATT AAC TTT CAG CGA GAT TCC TTT CTC AGG ATA GAT ATG TAT GCC ATG<br>Ile Asn Phe Gln Arg Asp Ser Phe Leu Arg Ile Asp Met Tyr Ala Met<br>                  375                   380               385 | 1628 |
| GGA CTG GTA CTC TGG GAA ATA GTA TCC CGA TGT ACA GCA GCA GAT GGG<br>Gly Leu Val Leu Trp Glu Ile Val Ser Arg Cys Thr Ala Ala Asp Gly<br>         390                    395                 400 | 1676 |
| CCA GTA GAT GAG TAT CTG CTC CCA TTC GAA GAA GAG ATT GGG CAA CAT<br>Pro Val Asp Glu Tyr Leu Leu Pro Phe Glu Glu Glu Ile Gly Gln His<br>         405                    410                 415 | 1724 |
| CCT TCC CTA GAG GAT CTG CAA GAA GTT GTC GTT CAC AAG AAG ATA CGC<br>Pro Ser Leu Glu Asp Leu Gln Glu Val Val Val His Lys Lys Ile Arg<br>420                   425                   430               435 | 1772 |
| CCT GTA TTC AAA GAC CAC TGG CTG AAA CAC CCT GGT CTG GCC CAA CTG<br>Pro Val Phe Lys Asp His Trp Leu Lys His Pro Gly Leu Ala Gln Leu<br>                  440                   445               450 | 1820 |

```
TGC GTC ACC ATT GAA GAA TGC TGG GAC CAT GAT GCG GAA GCA CGG CTT    1868
Cys Val Thr Ile Glu Glu Cys Trp Asp His Asp Ala Glu Ala Arg Leu
            455                 460                 465

TCG GCA GGC TGC GTA GAG GAG CGT ATT TCC CAA ATC CGT AAA TCA GTG    1916
Ser Ala Gly Cys Val Glu Glu Arg Ile Ser Gln Ile Arg Lys Ser Val
            470                 475                 480

AAC GGC ACT ACC TCG GAC TGC CTT GTA TCC ATT GTT ACA TCT GTC ACC    1964
Asn Gly Thr Thr Ser Asp Cys Leu Val Ser Ile Val Thr Ser Val Thr
            485                 490                 495

AAT GTG GAC TTG CCG CCC AAA GAG TCC AGT ATC TGAGGTTTCT TTGGTCTTTC   2017
Asn Val Asp Leu Pro Pro Lys Glu Ser Ser Ile
500                 505                 510

CAGACTCAGT GACTTTTAAA AAAAAAACTC ACGAATGCAG CTGCTATTTT ATCTTGACTT   2077

TTTAATATTT TTTTTCTTGG ATTTTACTTG GATCGGATCA ATTTACCAGC ACGTCATTCG   2137

AAAGTATTAA AAAAAAAAAA CAAAACAAAA AAGCAAAAAC AGACATCTCA GCAAGCATTC   2197

AGGTGCCGAC TTATGAATGC CAATAGGTGC AGGAACTTCA GAACCTCAAC AAAACTCATTT  2257

CTAGAGAATG TTCTCCTGGT TTCCTTTATC TCAGAAGAGG ACCCATAGGA AAACACCTAA   2317

GTCAAGCAAA TGCTGCAG                                                2335

(2) INFORMATION FOR SEQ ID NO: 4:

(i) SEQUENCE CHARACTERISTICS:
        (A) LENGTH: 510 amino acids
        (B) TYPE: amino acid
        (D) TOPOLOGY: linear (ii) MOLECULE TYPE: protein (xi) SEQUENCE DESCRIPTION: SEQ ID NO: 4:

Met Gly Ala Ser Val Ala Leu Thr Phe Leu Leu Leu Ala Thr Phe
 1               5                  10                  15

Arg Ala Gly Ser Gly His Asp Glu Val Glu Thr Arg Glu Cys Ile Tyr
                20                  25                  30

Tyr Asn Ala Asn Trp Glu Leu Glu Lys Thr Asn Gln Ser Gly Val Glu
            35                  40                  45

Ser Cys Glu Gly Glu Lys Asp Lys Arg Leu His Cys Tyr Ala Ser Trp
    50                  55                  60

Arg Asn Asn Ser Gly Phe Ile Glu Leu Val Lys Lys Gly Cys Trp Leu
65                  70                  75                  80

Asp Asp Phe Asn Cys Tyr Asp Arg Gln Glu Cys Ile Ala Lys Glu Glu
                85                  90                  95

Asn Pro Gln Val Phe Phe Cys Cys Cys Glu Gly Asn Tyr Cys Asn Lys
            100                 105                 110

Lys Phe Thr His Leu Pro Glu Val Glu Thr Phe Asp Pro Lys Pro Gln
        115                 120                 125

Pro Ser Ala Ser Val Leu Asn Ile Leu Ile Tyr Ser Leu Leu Pro Ile
    130                 135                 140

Val Gly Leu Ser Met Ala Ile Leu Leu Ala Phe Trp Met Tyr Arg His
145                 150                 155                 160

Arg Lys Pro Pro Tyr Gly His Val Glu Ile Asn Glu Asp Pro Gly Leu
                165                 170                 175

Pro Pro Pro Ser Pro Leu Val Gly Leu Lys Pro Leu Gln Leu Leu Glu
            180                 185                 190

Ile Lys Ala Arg Gly Arg Phe Gly Cys Val Trp Lys Ala Arg Leu Leu
        195                 200                 205
```

```
Asn Glu Tyr Val Ala Val Lys Ile Phe Pro Val Gln Asp Lys Gln Ser
    210                 215                 220

Trp Gln Cys Glu Lys Glu Ile Phe Thr Thr Pro Gly Met Lys His Glu
225                 230                 235                 240

Asn Leu Leu Glu Phe Ile Ala Ala Glu Lys Arg Gly Ser Asn Leu Glu
                245                 250                 255

Met Glu Leu Trp Leu Ile Thr Ala Phe His Asp Lys Gly Ser Leu Thr
            260                 265                 270

Asp Tyr Leu Lys Gly Asn Leu Val Ser Trp Asn Glu Leu Cys His Ile
        275                 280                 285

Thr Glu Thr Met Ala Arg Gly Leu Ala Tyr Leu His Glu Asp Val Pro
    290                 295                 300

Arg Cys Lys Gly Glu Gly His Lys Pro Ala Ile Ala His Arg Asp Phe
305                 310                 315                 320

Lys Ser Lys Asn Val Leu Leu Arg Asn Asp Leu Thr Ala Ile Leu Ala
                325                 330                 335

Asp Phe Gly Leu Ala Val Arg Phe Glu Pro Gly Lys Pro Pro Gly Asp
            340                 345                 350

Thr His Gly Gln Val Gly Thr Arg Arg Tyr Met Ala Pro Glu Val Leu
            355                 360                 365

Glu Gly Ala Ile Asn Phe Gln Arg Asp Ser Phe Leu Arg Ile Asp Met
370                 375                 380

Tyr Ala Met Gly Leu Val Leu Trp Glu Ile Val Ser Arg Cys Thr Ala
385                 390                 395                 400

Ala Asp Gly Pro Val Asp Glu Tyr Leu Leu Pro Phe Glu Glu Glu Ile
                405                 410                 415

Gly Gln His Pro Ser Leu Glu Asp Leu Gln Glu Val Val Val His Lys
            420                 425                 430

Lys Ile Arg Pro Val Phe Lys Asp His Trp Leu Lys His Pro Gly Leu
        435                 440                 445

Ala Gln Leu Cys Val Thr Ile Glu Glu Cys Trp Asp His Asp Ala Glu
450                 455                 460

Ala Arg Leu Ser Ala Gly Cys Val Glu Glu Arg Ile Ser Gln Ile Arg
465                 470                 475                 480

Lys Ser Val Asn Gly Thr Thr Ser Asp Cys Leu Val Ser Ile Val Thr
                485                 490                 495

Ser Val Thr Asn Val Asp Leu Pro Pro Lys Glu Ser Ser Ile
            500                 505                 510

(2) INFORMATION FOR SEQ ID NO: 5:

(i) SEQUENCE CHARACTERISTICS:
        (A) LENGTH: 6 amino acids
        (B) TYPE: amino acid
        (D) TOPOLOGY: both (ii) MOLECULE TYPE: protein (v) FRAGMENT TYPE: internal (xi) SEQUENCE DESCRIPTION: SEQ ID NO: 5:

Asp Leu Lys Pro Glu Asn
1               5

(2) INFORMATION FOR SEQ ID NO: 6:

(i) SEQUENCE CHARACTERISTICS:
        (A) LENGTH: 6 amino acids
```

```
         (B) TYPE: amino acid
         (D) TOPOLOGY: both (ii) MOLECULE TYPE: protein (v) FRAGMENT TYPE: internal (ix) FEATURE:
         (A) NAME/KEY: Modified-site
         (B) LOCATION: 2
         (D) OTHER INFORMATION: /note= "Xaa at position 2 is either
             "Thr" or "Ser"."

(ix) FEATURE:
         (A) NAME/KEY: Modified-site
         (B) LOCATION: 5
         (D) OTHER INFORMATION: /note= "Xaa a position 5 is either
             "Tyr" or "Phe"."

(xi) SEQUENCE DESCRIPTION: SEQ ID NO: 6:

Gly Xaa Xaa Xaa Xaa Xaa
1               5

(2) INFORMATION FOR SEQ ID NO: 7:

(i) SEQUENCE CHARACTERISTICS:
         (A) LENGTH: 6 amino acids
         (B) TYPE: amino acid
         (D) TOPOLOGY: both (ii) MOLECULE TYPE: protein (v) FRAGMENT TYPE: internal (xi) SEQUENCE DESCRIPTION: SEQ ID NO: 7:

Asp Ile Lys Ser Lys Asn
1               5

(2) INFORMATION FOR SEQ ID NO: 8:

(i) SEQUENCE CHARACTERISTICS:
         (A) LENGTH: 6 amino acids
         (B) TYPE: amino acid
         (D) TOPOLOGY: both (ii) MOLECULE TYPE: protein (v) FRAGMENT TYPE: internal (xi) SEQUENCE DESCRIPTION: SEQ ID NO: 8:

Gly Thr Arg Arg Tyr Met
1               5

(2) INFORMATION FOR SEQ ID NO: 9:

(i) SEQUENCE CHARACTERISTICS:
         (A) LENGTH: 6 amino acids
         (B) TYPE: amino acid
         (D) TOPOLOGY: unknown (ii) MOLECULE TYPE: protein (v) FRAGMENT TYPE: internal (xi) SEQUENCE DESCRIPTION: SEQ ID NO: 9:

Asp Leu Ala Ala Arg Asn
1               5

(2) INFORMATION FOR SEQ ID NO: 10:

(i) SEQUENCE CHARACTERISTICS:
```

(A) LENGTH: 6 amino acids
          (B) TYPE: amino acid
          (D) TOPOLOGY: both (ii) MOLECULE TYPE: protein (v) FRAGMENT TYPE: internal (ix) FEATURE:
          (A) NAME/KEY: Modified-site
          (B) LOCATION: 3
          (D) OTHER INFORMATION: /note= "Xaa at position 3 is either
              "Ile" or "Val"."

(ix) FEATURE:
          (A) NAME/KEY: Modified-site
          (B) LOCATION: 4
          (D) OTHER INFORMATION: /note= "Xaa at position 4 is either
              "Lys" or "Arg"."

(ix) FEATURE:
          (A) NAME/KEY: Modified-site
          (B) LOCATION: 6
          (D) OTHER INFORMATION: /note= "Xaa at position 6 is either
              "Thr" or "Met"."

(xi) SEQUENCE DESCRIPTION: SEQ ID NO: 10:

Xaa Pro Xaa Xaa Trp Xaa
1               5

(2) INFORMATION FOR SEQ ID NO: 11:

(i) SEQUENCE CHARACTERISTICS:
          (A) LENGTH: 1602 base pairs
          (B) TYPE: nucleic acid
          (C) STRANDEDNESS: both
          (D) TOPOLOGY: both (ii) MOLECULE TYPE: cDNA (ix) FEATURE:
          (A) NAME/KEY: CDS
          (B) LOCATION: 72..1553

(xi) SEQUENCE DESCRIPTION: SEQ ID NO: 11:

CCCCGGGAAC TTCAAAGCGC GCTGCGGCGG CGCTCTGGGA CCCCGAAGCC TTGCACCGCC      60

GCGGGGTGGC C ATG ACC CCA GCG CGC CGC TCC GCA CTG AGC CTG GCC CTC     110
             Met Thr Pro Ala Arg Arg Ser Ala Leu Ser Leu Ala Leu
               1               5                  10

CTG CTG GTG GCA CTG GCC TCC GAC CTT GCG GCA GGA CTG AAG TGT GTG     158
Leu Leu Val Ala Leu Ala Ser Asp Leu Ala Ala Gly Leu Lys Cys Val
     15                  20                  25

TGT CTT TTG TGT GAT TCC TCA AAC TTT ACC TGC CAA ACC GAA GGA GCA     206
Cys Leu Leu Cys Asp Ser Ser Asn Phe Thr Cys Gln Thr Glu Gly Ala
 30                  35                  40                  45

TGC TGG GCC TCT GTC ATG CTA ACC AAC GGG AAA GAA CAG GTG AGC AAA     254
Cys Trp Ala Ser Val Met Leu Thr Asn Gly Lys Glu Gln Val Ser Lys
             50                  55                  60

TCG TGC GTG TCC CTC CCG GAA CTA AAT GCT CAG GTC TTC TGT CAC AGT     302
Ser Cys Val Ser Leu Pro Glu Leu Asn Ala Gln Val Phe Cys His Ser
         65                  70                  75

TCC AAC AAC GTG ACC AAG ACC GAA TGT TGC TTC ACA GAC TTC TGC AAC     350
Ser Asn Asn Val Thr Lys Thr Glu Cys Cys Phe Thr Asp Phe Cys Asn
     80                  85                  90

AAC ATC ACT CAG CAC CTT CCC ACA GCA TCT CCA GAT GCC CCT AGA CTT     398
Asn Ile Thr Gln His Leu Pro Thr Ala Ser Pro Asp Ala Pro Arg Leu
 95                 100                 105

GGC CCC ACA GAG CTG ACA GTT GTT ATC ACT GTA CCT GTT TGC CTC CTG     446

|  |  |
|---|---|
| Gly Pro Thr Glu Leu Thr Val Val Ile Thr Val Pro Val Cys Leu Leu<br>110     115      120    125 | |
| TCC ATC GCA GCC ATG CTA ACG ATA TGG GCC TGC CAG GAC CGC CAG TGC<br>Ser Ile Ala Ala Met Leu Thr Ile Trp Ala Cys Gln Asp Arg Gln Cys<br>         130      135      140 | 494 |
| ACA TAC AGG AAG ACC AAG AGA CAC AAT GTG GAG GAA CCA CTG GCA GAG<br>Thr Tyr Arg Lys Thr Lys Arg His Asn Val Glu Glu Pro Leu Ala Glu<br>     145      150      155 | 542 |
| TAC AGC CTT GTC AAT GCT GGA AAA ACC CTC AAA GAT CTG ATT TAT GAT<br>Tyr Ser Leu Val Asn Ala Gly Lys Thr Leu Lys Asp Leu Ile Tyr Asp<br>    160      165      170 | 590 |
| GCC ACT GCC TCG GGC TCA GGA TCT GGC CCG CCT CTT TTG GTT CAA AGA<br>Ala Thr Ala Ser Gly Ser Gly Ser Gly Pro Pro Leu Leu Val Gln Arg<br>175         180      185 | 638 |
| ACC ATC GCA AGG ACA ATT GTA CTT CAA GAA ATC GTA GGA AAA GGT CGG<br>Thr Ile Ala Arg Thr Ile Val Leu Gln Glu Ile Val Gly Lys Gly Arg<br>190         195      200      205 | 686 |
| TTT GGG GAA GTG TGG CAC GGA AGA TGG TGT GGA GAA GAT GTG GCT GTG<br>Phe Gly Glu Val Trp His Gly Arg Trp Cys Gly Glu Asp Val Ala Val<br>         210      215      220 | 734 |
| AAA ATA TTC TCC TCC AGA GAT GAG AGA TCT TGG TTC CGT GAG GCA GAA<br>Lys Ile Phe Ser Ser Arg Asp Glu Arg Ser Trp Phe Arg Glu Ala Glu<br>     225      230      235 | 782 |
| ATT TAT CAG ACG GTA ATG CTG AGA CAT GAG AAT ATT CTC GGT TTC ATC<br>Ile Tyr Gln Thr Val Met Leu Arg His Glu Asn Ile Leu Gly Phe Ile<br>    240      245      250 | 830 |
| GCG GCC GAC AAC AAA GAT AAT GGA ACC TGG ACT CAG CTT TGG CTT GTG<br>Ala Ala Asp Asn Lys Asp Asn Gly Thr Trp Thr Gln Leu Trp Leu Val<br>255         260      265 | 878 |
| TCA GAG TAT CAC GAG CAG GGC TCC TTA TAT GAC TAT TTG AAT AGA AAC<br>Ser Glu Tyr His Glu Gln Gly Ser Leu Tyr Asp Tyr Leu Asn Arg Asn<br>270         275      280      285 | 926 |
| ATA GTG ACC GTG GCT GGA ATG GTC AAG TTG GCG CTT TCA ATA GCG AGT<br>Ile Val Thr Val Ala Gly Met Val Lys Leu Ala Leu Ser Ile Ala Ser<br>         290      295      300 | 974 |
| GGT CTG GCT CAC CTA CAC ATG GAG ATC GTG GGC ACT CAA GGT AAG CCT<br>Gly Leu Ala His Leu His Met Glu Ile Val Gly Thr Gln Gly Lys Pro<br>     305      310      315 | 1022 |
| GCT ATT GCT CAC CGA GAT ATA AAG TCA AAG AAT ATC TTA GTC AAA AAG<br>Ala Ile Ala His Arg Asp Ile Lys Ser Lys Asn Ile Leu Val Lys Lys<br>    320      325      330 | 1070 |
| TGT GAC ACT TGT GCC ATA GCT GAC TTA GGG CTG GCT GTG AAA CAT GAT<br>Cys Asp Thr Cys Ala Ile Ala Asp Leu Gly Leu Ala Val Lys His Asp<br>335         340      345 | 1118 |
| TCT ATC ATG AAC ACT ATA GAT ATA CCC CAG AAT CCT AAA GTG GGA ACC<br>Ser Ile Met Asn Thr Ile Asp Ile Pro Gln Asn Pro Lys Val Gly Thr<br>350         355      360      365 | 1166 |
| AAG AGG TAT ATG GCT CCC GAA ATG CTT GAT GAT ACA ATG AAC GTC AAC<br>Lys Arg Tyr Met Ala Pro Glu Met Leu Asp Asp Thr Met Asn Val Asn<br>         370      375      380 | 1214 |
| ATC TTT GAG TCC TTC AAG CGA GCT GAC ATC TAT TCG GTG GGG CTG GTT<br>Ile Phe Glu Ser Phe Lys Arg Ala Asp Ile Tyr Ser Val Gly Leu Val<br>     385      390      395 | 1262 |
| TAC TGG GAA ATA GCT CGA AGG TGT TCA GTT GGA GGA CTT GTT GAA GAG<br>Tyr Trp Glu Ile Ala Arg Arg Cys Ser Val Gly Gly Leu Val Glu Glu<br>    400      405      410 | 1310 |
| TAC CAG TTG CCT TAT TAT GAC ATG GTG CCT TCA GAT CCT TCC ATA GAG<br>Tyr Gln Leu Pro Tyr Tyr Asp Met Val Pro Ser Asp Pro Ser Ile Glu<br>415         420      425 | 1358 |

-continued

```
GAA ATG AGG AAG GTC GTT TGT GAT CAG AAA CTG CGA CCA AAT CTC CCA    1406
Glu Met Arg Lys Val Val Cys Asp Gln Lys Leu Arg Pro Asn Leu Pro
430             435                 440                 445

AAC CAG TGG CAA AGC TGT GAG GCG CTC CGG GTC ATG GGA AGA ATA ATG    1454
Asn Gln Trp Gln Ser Cys Glu Ala Leu Arg Val Met Gly Arg Ile Met
                450                 455                 460

CGT GAG TGC TGG TAT GCC AAC GGG GCA GCT CGC CTG ACC GCC CTG CGC    1502
Arg Glu Cys Trp Tyr Ala Asn Gly Ala Ala Arg Leu Thr Ala Leu Arg
            465                 470                 475

GTG AAG AAG ACC ATT TCT CAG CTG TGT GTC AAG GAA GAC TGT AAG GCC    1550
Val Lys Lys Thr Ile Ser Gln Leu Cys Val Lys Glu Asp Cys Lys Ala
        480                 485                 490

TAAGGATACA GGCGACGGGA AAGCCCTCAC CACTCTCTTT CATGTCTCCT GC          1602
```

(2) INFORMATION FOR SEQ ID NO: 12:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Thr Pro Ala Arg Arg Ser Ala Leu Ser Leu Ala Leu Leu Leu Val
 1               5                  10                  15

Ala Leu Ala Ser Asp Leu Ala Ala Gly Leu Lys Cys Val Cys Leu Leu
                20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ser Lys Ser Cys Val
        50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Gln His Leu Pro Thr Ala Ser Pro Asp Ala Pro Arg Leu Gly Pro Thr
            100                 105                 110

Glu Leu Thr Val Val Ile Thr Val Pro Val Cys Leu Leu Ser Ile Ala
        115                 120                 125

Ala Met Leu Thr Ile Trp Ala Cys Gln Asp Arg Gln Cys Thr Tyr Arg
    130                 135                 140

Lys Thr Lys Arg His Asn Val Glu Glu Pro Leu Ala Glu Tyr Ser Leu
145                 150                 155                 160

Val Asn Ala Gly Lys Thr Leu Lys Asp Leu Ile Tyr Asp Ala Thr Ala
                165                 170                 175

Ser Gly Ser Gly Ser Gly Pro Pro Leu Leu Val Gln Arg Thr Ile Ala
            180                 185                 190

Arg Thr Ile Val Leu Gln Glu Ile Val Gly Lys Gly Arg Phe Gly Glu
        195                 200                 205

Val Trp His Gly Arg Trp Cys Gly Glu Asp Val Ala Val Lys Ile Phe
    210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
```

```
                 260             265             270
His Glu Gln Gly Ser Leu Tyr Asp Tyr Leu Asn Arg Asn Ile Val Thr
            275             280             285

Val Ala Gly Met Val Lys Leu Ala Leu Ser Ile Ala Ser Gly Leu Ala
        290             295             300

His Leu His Met Glu Ile Val Gly Thr Gln Gly Lys Pro Ala Ile Ala
305             310             315             320

His Arg Asp Ile Lys Ser Lys Asn Ile Leu Val Lys Lys Cys Asp Thr
            325             330             335

Cys Ala Ile Ala Asp Leu Gly Leu Ala Val Lys His Asp Ser Ile Met
            340             345             350

Asn Thr Ile Asp Ile Pro Gln Asn Pro Lys Val Gly Thr Lys Arg Tyr
            355             360             365

Met Ala Pro Glu Met Leu Asp Asp Thr Met Asn Val Asn Ile Phe Glu
        370             375             380

Ser Phe Lys Arg Ala Asp Ile Tyr Ser Val Gly Leu Val Tyr Trp Glu
385             390             395             400

Ile Ala Arg Arg Cys Ser Val Gly Gly Leu Val Glu Glu Tyr Gln Leu
                405             410             415

Pro Tyr Tyr Asp Met Val Pro Ser Asp Pro Ser Ile Glu Glu Met Arg
            420             425             430

Lys Val Val Cys Asp Gln Lys Leu Arg Pro Asn Leu Pro Asn Gln Trp
            435             440             445

Gln Ser Cys Glu Ala Leu Arg Val Met Gly Arg Ile Met Arg Glu Cys
        450             455             460

Trp Tyr Ala Asn Gly Ala Ala Arg Leu Thr Ala Leu Arg Val Lys Lys
465             470             475             480

Thr Ile Ser Gln Leu Cys Val Lys Glu Asp Cys Lys Ala
            485             490

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

CGGGATCCGT NGCNGTNAAR ATHTTYCC                                    28

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CGGGATCCYT CNGGNGCCAT RTANCKYCTN GTNCC                            35
```